(12) United States Patent
Jackson et al.

(10) Patent No.: US 12,370,554 B2
(45) Date of Patent: Jul. 29, 2025

(54) SYSTEM AND METHOD FOR WASTE VOLUME REDUCTION AND CAPTURE

(71) Applicant: Mobi Waste Inc., Danbury, TX (US)

(72) Inventors: Donna K. Jackson, Duncan, OK (US); Justin Lane Richardson, Danbury, TX (US)

(73) Assignee: MOBI WASTE INC., Danbury, TX (US)

( * ) Notice: Subject to any disclaimer, the term of this patent is extended or adjusted under 35 U.S.C. 154(b) by 0 days.

(21) Appl. No.: 18/981,068

(22) Filed: Dec. 13, 2024

(65) Prior Publication Data

US 2025/0196154 A1 Jun. 19, 2025

Related U.S. Application Data

(60) Provisional application No. 63/610,932, filed on Dec. 15, 2023.

(51) Int. Cl.
*B02C 18/22* (2006.01)
*A61L 2/16* (2006.01)
(Continued)

(52) U.S. Cl.
CPC ............ *B02C 18/2291* (2013.01); *A61L 2/16* (2013.01); *B02C 18/12* (2013.01); *A61L 2202/15* (2013.01); *B02C 19/0081* (2013.01)

(58) Field of Classification Search
CPC ......... B02C 23/20; B02C 23/18; B02C 18/22; B02C 18/2225; B02C 18/2291;
(Continued)

(56) References Cited

U.S. PATENT DOCUMENTS 5,474,239 A 12/1995 Williams et al.
5,860,606 A * 1/1999 Tiedeman ........... B02C 18/2291
241/285.2
(Continued)

FOREIGN PATENT DOCUMENTS

PH 2016/000362 A1 9/2017
PH 12016000362 A1 * 10/2017
(Continued)

OTHER PUBLICATIONS

USPTO Acting as The International Searching Authority; International Search Report and Written Opinion regarding PCT/US2024/060171; Mailed Feb. 27, 2025.

*Primary Examiner* — Bobby Yeonjin Kim
(74) *Attorney, Agent, or Firm* — DUNLAP CODDING, P.C.

(57) ABSTRACT

Systems and methods for waste volume reduction and disposal, including a system comprising a feeder chute rotatable about a first axis; a shredder assembly comprising a housing configured to accept waste from the feeder chute and a shaft within the housing rotatable about a second axis; a plurality of blades attached to the shaft so as to shred the waste into shredded pieces; and a plurality of cleaning arms positioned such that at least a portion of the plurality of blades passes between two or more of the cleaning arms when the plurality of blades is rotated within the housing by the shaft; an agent reservoir positioned proximate to the shredder assembly and configured to contain and disperse agent(s); and an exit chute having an entry end aligned with the bottom of the housing so as to accept and dispense the shredded pieces of waste.

18 Claims, 29 Drawing Sheets

(51) Int. Cl.
*B02C 18/12* (2006.01)
*B02C 19/00* (2006.01)

(58) Field of Classification Search
CPC ......... B02C 18/06; B02C 18/18; B02C 18/14;
B02C 18/2216; B02C 19/00; B02C 19/18;
B02C 19/0075
See application file for complete search history.

(56) References Cited

U.S. PATENT DOCUMENTS

| | | | |
|---|---|---|---|
| 6,186,428 B1 * | 2/2001 | Robinson | B02C 19/186 |
| | | | 241/73 |
| 11,673,144 B1 | 6/2023 | Messinger | |
| 2008/0213124 A1 * | 9/2008 | Hengl | B02C 19/0075 |
| | | | 422/301 |
| 2014/0014755 A1 | 1/2014 | Taylor | |
| 2015/0273476 A1 | 10/2015 | Jackson | |
| 2018/0361390 A1 | 12/2018 | Jackson | |
| 2020/0055057 A1 | 2/2020 | Stahl | |
| 2021/0053071 A1 | 2/2021 | Kemp et al. | |

FOREIGN PATENT DOCUMENTS

| | | | | |
|---|---|---|---|---|
| WO | WO 2012/095750 A1 | 7/2012 | | |
| WO | WO-2012095750 A2 * | 7/2012 | ........... | B02C 21/026 |

\* cited by examiner

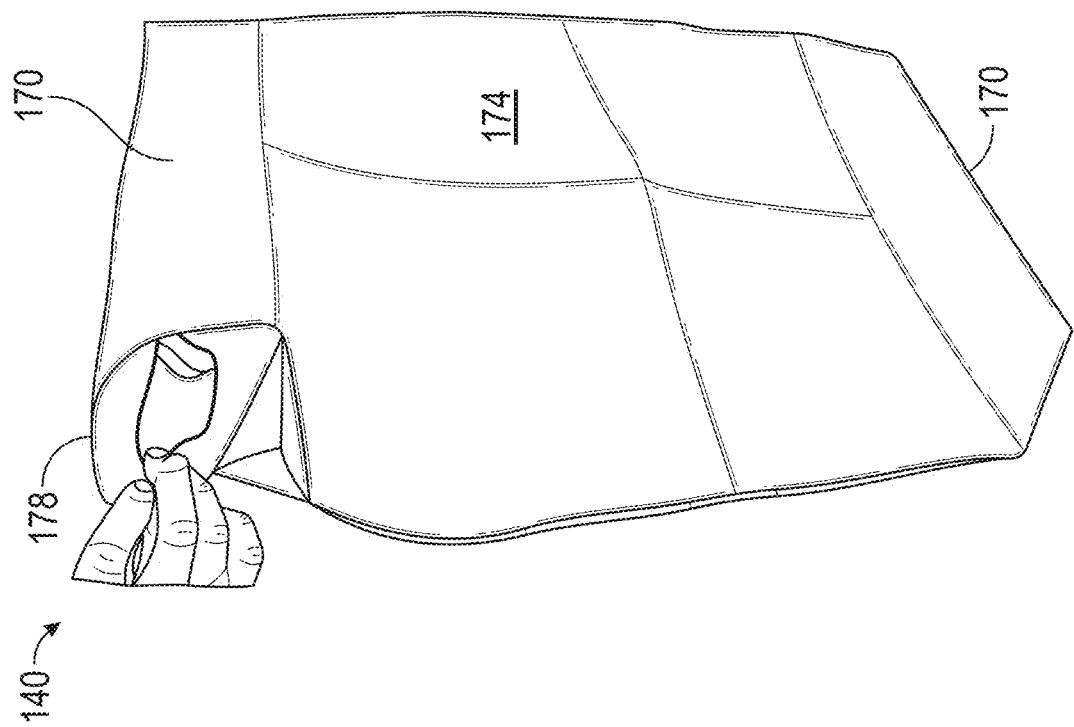
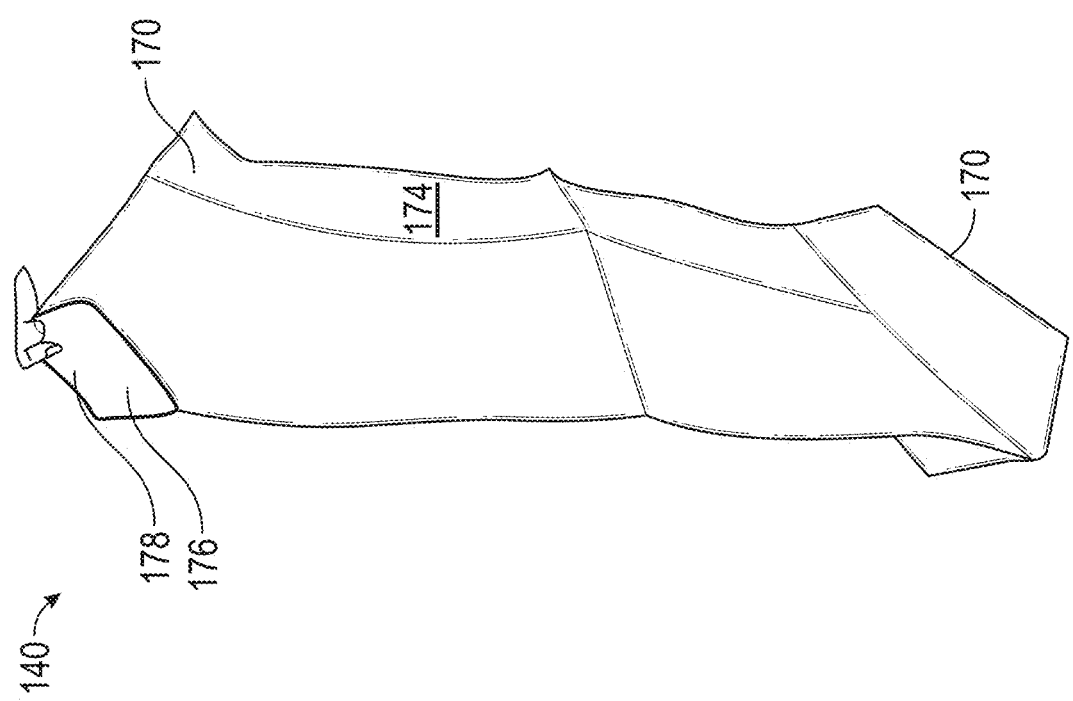

SYSTEM AND METHOD FOR WASTE VOLUME REDUCTION AND CAPTURE

CROSS-REFERENCE TO RELATED APPLICATIONS

This application claims priority to U.S. provisional application No. 63/610,932, entitled "SYSTEM AND METHOD FOR WASTE VOLUME REDUCTION AND CAPTURE", filed on Dec. 15, 2023, the entire contents of which are hereby incorporated by reference in their entirety herein.

FIELD OF THE DISCLOSURE

The disclosure generally relates to systems and methods and apparatuses that reduce the volume of waste and capture the reduced-volume waste. More particularly the disclosure relates to systems and methods that shred waste into shredded pieces to eliminate or reduce the volume of the waste.

BACKGROUND

Traditionally, waste disposal largely comprises the collection and disposal of loose trash in trash bags and transporting the bags of trash to a disposal site, like a landfill. The loose trash is generally collected in the form in which it was found and is not broken down before disposal. Trash in this form generally consumes a disproportionately large amount of space, both at collection and at disposal sites. This inefficiency results in increased transportation costs, including additional fuel, manpower, and equipment, as fewer items can be transported per trip. Trash that is not broken down before disposal also accelerates the rate at which landfill space is used and takes longer to decompose than waste broken into smaller pieces.

Further, current systems that shred or crush waste typically require transport of the waste to the equipment and/or are not immediately available.

Thus, a need exists for a new and improved system that is configured to reduce the volume of collected waste to improve storage, recycling, transportation, disposal, and decomposition of the waste. Further, a need exists for onsite systems for immediate reduction of waste volume. It is to such systems, and methods of producing and using the same, that the present disclosure is directed.

SUMMARY OF THE DISCLOSURE

The problems involved in collection and disposal of whole trash is solved by systems and methods for waste volume reduction and capture. In one embodiment, a waste-volume reduction system, may comprise: a feeder chute having an intake end, an output end, an interior, and an exterior, the feeder chute configured to channel waste through the interior, wherein at least the intake end of the feeder chute is rotatable about a first axis; a shredder assembly, the shredder assembly comprising: a housing having a length, a top having a first opening, a bottom having a second opening, and a wall extending between the top and the bottom, wherein the first opening of the top is positioned proximate to the output end of the feeder chute and aligned with at least a portion of the interior of the feeder chute so as to accept waste from the feeder chute. The system may further comprise a shaft extending within the housing along the length of the housing, the shaft rotatable about a second axis, the shaft positioned between the top and the bottom of the housing. The system may comprise a plurality of blades attached to the shaft, the plurality of blades comprising at least a first blade and a second blade, wherein the first blade is rotationally offset about the second axis on the shaft from the second blade, so as to shred the waste into shredded pieces when the shaft rotates. The system may comprise a plurality of cleaning arms attached to the interior of the housing and positioned such that at least a portion of the plurality of blades passes between two or more of the cleaning arms when the plurality of blades is rotated within the housing by the shaft. The system may comprise an agent reservoir positioned proximate to the shredder assembly and configured to contain one or more anti-microbial agents and/or anti-bacterial agents, the agent reservoir having an applicator configured to disperse the one or more anti-microbial agents and/or anti-bacterial agents from the agent reservoir onto the shredded pieces of waste. The system may comprise an exit chute having an entry end aligned with the second opening of the bottom of the housing of the shredder assembly so as to accept the shredded pieces of waste from the shredder assembly, the exit chute having an exit end configured to dispense the shredded pieces of waste.

In some embodiments, a method for waste-volume reduction may comprise feeding waste into a feeder chute having an intake end, an output end, an interior, and an exterior, the feeder chute configured to channel the waste through the interior, wherein at least the intake end of the feeder chute is rotatable about a first axis; shredding the waste into shredded pieces of waste with a shredder assembly, the shredder assembly comprising: a housing having a length, a top having a first opening, a bottom having a second opening, and a wall extending between the top and the bottom, wherein the first opening of the top is positioned proximate to the output end of the feeder chute and aligned with at least a portion of the interior of the feeder chute so as to accept the waste from the feeder chute; a shaft extending within the housing along the length of the housing, the shaft rotatable about a second axis, the shaft positioned between the top and the bottom of the housing; a plurality of blades attached to the shaft, the plurality of blades comprising at least a first blade and a second blade, wherein the first blade is rotationally offset about the second axis on the shaft from the second blade, so as to shred the waste into shredded pieces when the shaft rotates; and a plurality of cleaning arms attached to the interior of the housing and positioned such that at least a portion of the plurality of blades passes between two or more of the cleaning arms when the plurality of blades is rotated within the housing by the shaft. The method may comprise dispersing one or more anti-microbial agents and/or anti-bacterial agents from a reservoir positioned proximate to the shredder assembly, the reservoir having an applicator configured to disperse the one or more anti-microbial agents and/or anti-bacterial agents from the reservoir onto the shredded pieces of waste. The method may further comprise dispensing the shredded pieces of waste from an exit chute having an entry end aligned with the second opening of the bottom of the housing of the shredder assembly so as to accept the shredded pieces of waste from the shredder assembly, the exit chute having an exit end configured to dispense the shredded pieces of waste.

BRIEF DESCRIPTION OF THE DRAWINGS

The accompanying drawings, which are incorporated in and constitute a part of this specification, illustrate one or more embodiments described herein. The drawings are not intended to be drawn to scale, and certain features and certain views of the figures may be shown exaggerated, to scale or in schematic in the interest of clarity and conciseness. Not every component may be labeled in every drawing. Like reference numerals in the figures may represent and refer to the same or similar element or function and a detailed description of like reference numerals varying only in alphabetical suffix may be omitted for conciseness unless otherwise specified. In the drawings:

FIG. 15A is a side perspective view of an exemplary collection bag in accordance with the present disclosure.

FIG. 15B is a front perspective view of the exemplary collection bag of FIG. 15A.

DETAILED DESCRIPTION

Figure 1:
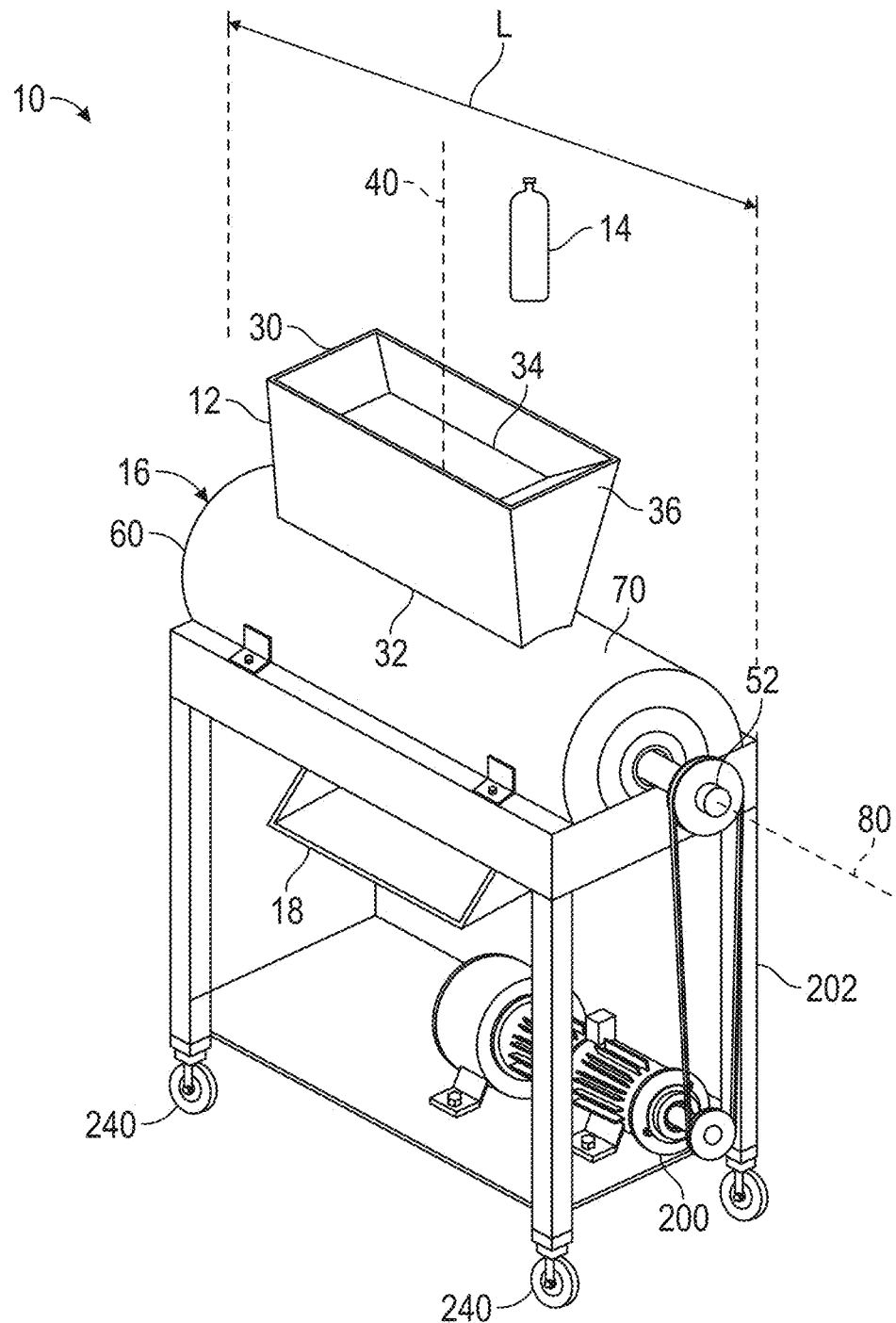
FIG. 1 is a perspective view of an exemplary waste-volume reduction system in accordance with the present disclosure.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways.

Headings are provided for convenience only and are not to be construed to limit the disclosure in any manner. Embodiments illustrated under any heading or in any portion of the disclosure may be combined with embodiments illustrated under the same or any other heading or other portion of the disclosure. Any combination of the elements described herein in all possible variations thereof is encompassed by the disclosure unless otherwise indicated herein or otherwise clearly contradicted by context.

Unless otherwise required by context, singular terms shall include pluralities and plural terms shall include the singular.

All of the compositions, assemblies, systems, kits, and/or methods disclosed herein can be made and executed without undue experimentation in light of the present disclosure. Where a method claim does not specifically state in the claims or description that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of embodiments described in the specification.

In addition, use of the "a" or "an" are employed to describe elements and components of the embodiments herein. This is done merely for convenience and to give a general sense of the inventive concept. This description should be read to include one or more and the singular also includes the plural unless it is obvious that it is meant otherwise. The term "plurality" refers to "two or more" unless expressly stated to the contrary.

As used herein, qualifiers like "substantially," "about," "approximately," and combinations and variations thereof, are intended to include not only the exact amount or value that they qualify, but also some slight deviations therefrom, which may be due to manufacturing tolerances, measurement error, wear and tear, stresses exerted on various parts, and combinations thereof, for example.

Further, the phrase "based on" is intended to mean "based, at least in part, on" unless explicitly stated otherwise.

In addition, the use of the term "at least one of X, Y, and Z" will be understood to include X alone, Y alone, and Z alone, as well as any combination of X, Y, and Z. The use of ordinal number terminology (e.g., "first," "second," "third," "fourth," etc.) is solely for the purpose of differentiating between two or more items and is not meant to imply any sequence or order or importance to one item over another or any order of addition, for example.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

Circuitry, as used herein, may be analog and/or digital components, or one or more suitably programmed processors (e.g., microprocessors) and associated hardware and software, or hardwired logic. Also, "computer components" may perform one or more functions. The term "computer component," may include hardware, such as a processor (e.g., microprocessor), an application specific integrated circuit (ASIC), a field programmable gate array (FPGA), a combination of hardware and software, and/or the like. The term "processor" as used herein means a single processor or multiple processors working independently or together to collectively perform a task.

As used herein, all numerical values or ranges include fractions of the values and integers within such ranges and fractions of the integers within such ranges unless the context clearly indicates otherwise. The numerical ranges specified herein include the endpoints, and all values, sub-ranges of values within the range, and fractions of the values and integers within said range. Thus, any two values within the range of 1 mm to 10 m, for example, can be used to set a lower and an upper boundary of a range in accordance with the embodiments of the present disclosure.

Figure 2:
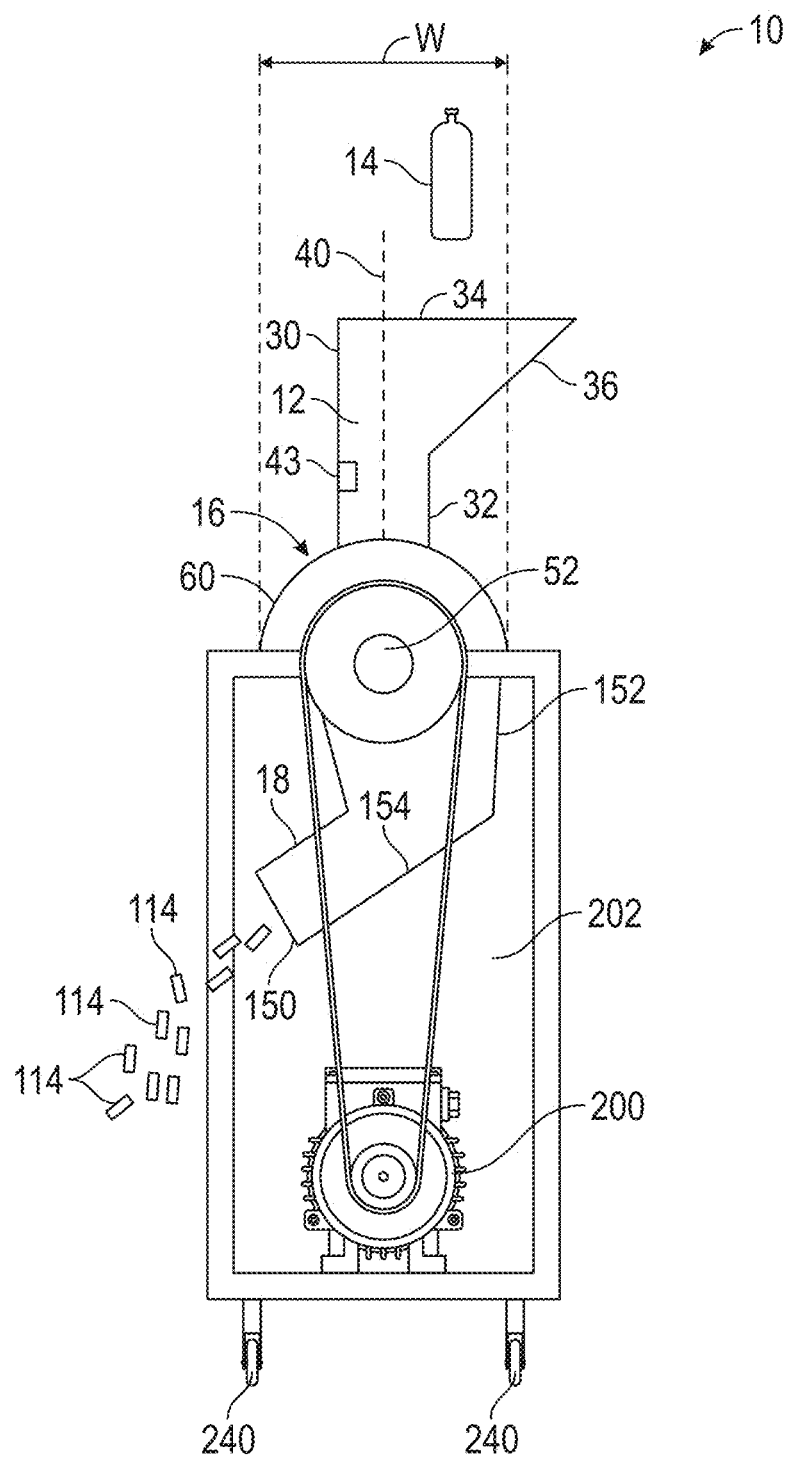
FIG. 2 is a side view of the exemplary waste volume reduction system of FIG. 1.

Referring now to the drawings and in particular to FIGS. 1 and 2, shown therein is an exemplary embodiment of a waste-volume reduction system 10. In general, the waste-volume reduction system 10 may comprise a feeder chute 12 configured to accept and direct the waste 14 into a shredder assembly 16. The shredder assembly 16 is configured to shred the waste 14 and direct a plurality of shredded pieces 114 of the waste 14 into an exit chute 18. The feeder chute 12 may be rotatable in order to better accept and direct the waste 14. The waste-volume reduction system 10 may further comprise an additive reservoir 20 (FIG. 8) for dispensing one or more additive 22, such as one or more anti-microbial and/or anti-bacterial agents 22, into the shredder assembly 16 and/or into/on the shredded pieces 114 of the waste 14.

The waste 14 may include one or more of metal, plastic, food, cardboard, paper, mixed-media, diapers, vegetation, wood, and other waste. In some embodiments, the shredded pieces 114 of the waste 14 may have a length in a range between 0.1 inch and twelve inches long. The shredded pieces 114 of the waste 14 may have a width in a range between 0.1 inch and twelve inches wide. The shredded pieces 114 of the waste 14 may have a thickness in a range between 0.1 inch and twelve inches thick. In some embodiments, the shredded pieces 114 of the waste 14 may have sizes depending on the type of material within the waste 14. For example, when the waste 14 comprises one or more of diapers and aluminum cans, the shredded pieces 114 may have sizes that are may be longer, thinner, and wider than for other types of waste. In some embodiments, the shredded pieces 114 of the waste 14 may be variable in size.

In some embodiments, the feeder chute 12 may have an intake end 30, an output end 32, an interior 34, and an exterior 36. The feeder chute 12 may be configured to channel the waste 14 through the interior 34 of the feeder chute 12. In some embodiments, at least the intake end 30 of the feeder chute 12 is rotatable about a first axis 40.

Figure 3:
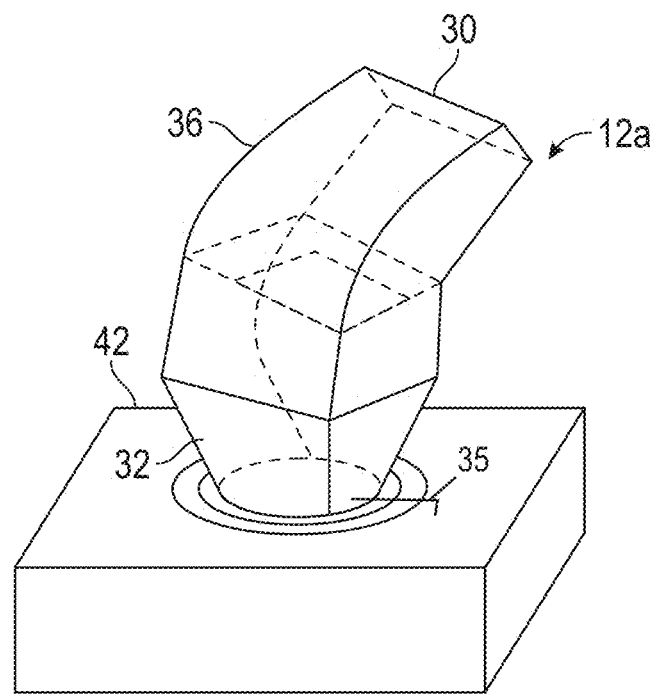
FIG. 3 is a perspective view of an exemplary feeder chute of the waste-volume reduction system in accordance with the present disclosure.
Figure 4:
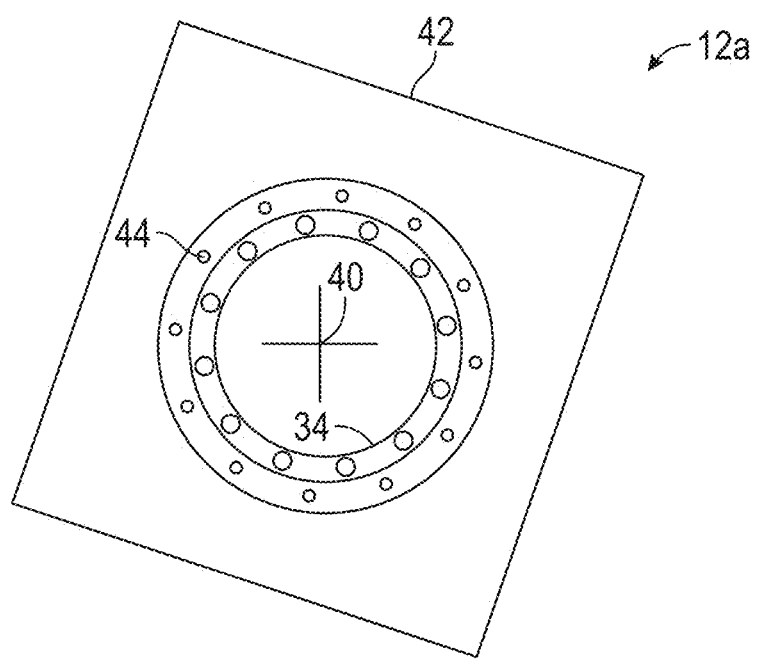
FIG. 4 is a top plan view of components of the exemplary feeder chute of FIG. 3.

As illustrated in FIGS. 3 and 4, in some embodiments the waste-volume reduction system 10 may include an exemplary feeder chute 12a, which may be rotatably connected to a stationary plate 42. The output end 32 of the feeder chute 12a may include two or more ball bearings 44, for instance. In some embodiments, the feeder chute 12, 12a, or at least the intake end 30 of the feeder chute 12, 12a, may be rotatable at an angle to the first axis 40, such that at least the intake end 30 of the feeder chute 12, 12a is movable in two or three dimensions, in order to accept waste into the interior 34 of the feeder chute 12, 12a from multiple directions.

In some embodiments, the output end 32 of the feeder chute 12, 12a comprises, or is engageable with, one or more of the ball bearings 44 such that at least the intake end 30 of the feeder chute is rotatable about the first axis 40.

In some embodiments, the output end 32 of the feeder chute 12, 12a comprises or is engageable with one or more lock 35 that is configured to lock the feeder chute 12, 12a into place rotationally. The lock 35 may be one or more of a stopper, a connector, a latch, a sliding lock, a pin and receiver, or other stopping mechanism. The lock 35 may be positioned externally to the feeder chute 12, 12a, internally in the feeder chute 12, 12, or embedded or partially embedded in the feeder chute 12, 12a. The lock 35 is configured to secure the intake end 30 of the feeder chute 12, 12a into a desired rotational position.

Figure 20:
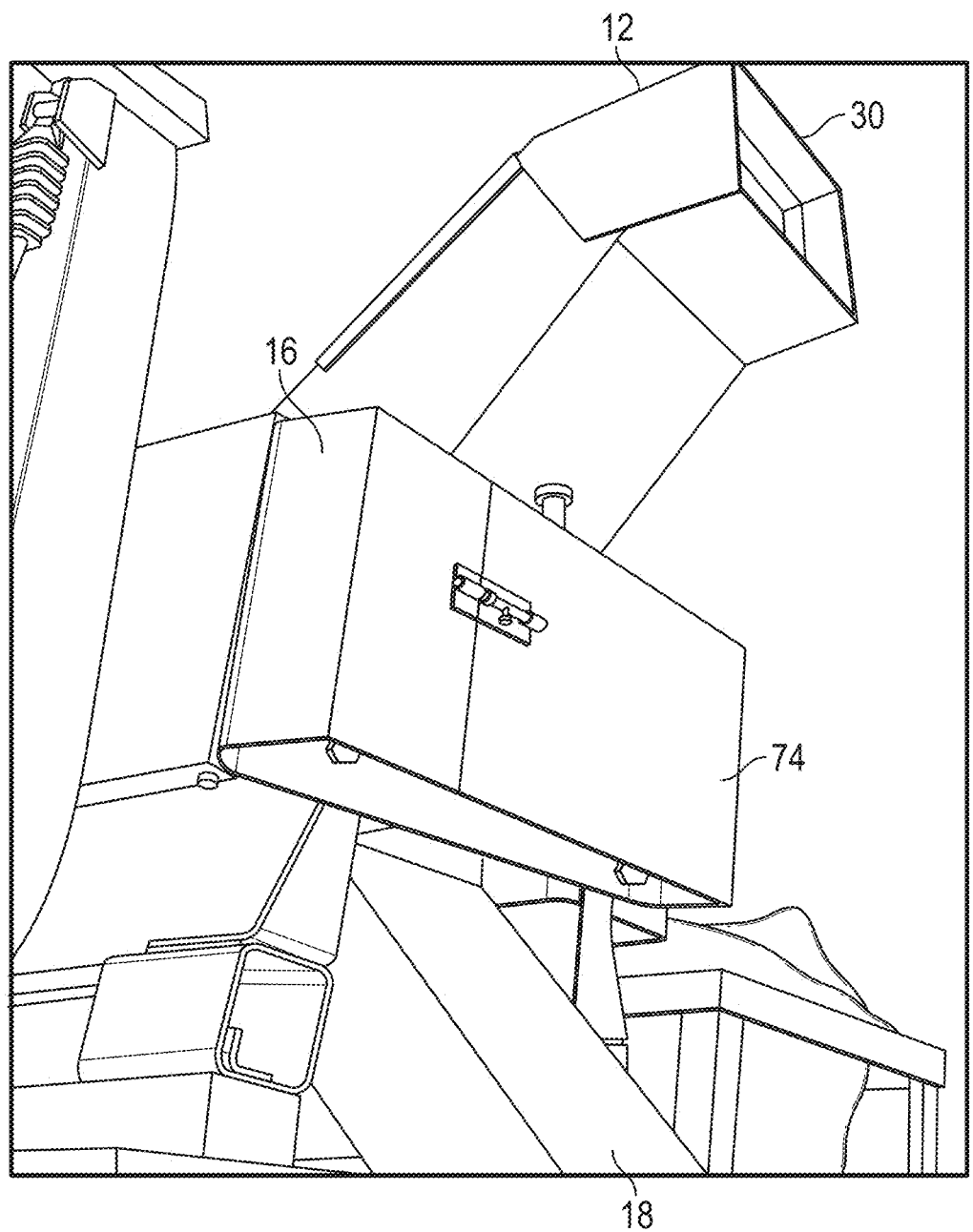
FIG. 20 is a perspective view of the components of the waste-volume reduction system of FIG. 17.
Figure 21B:
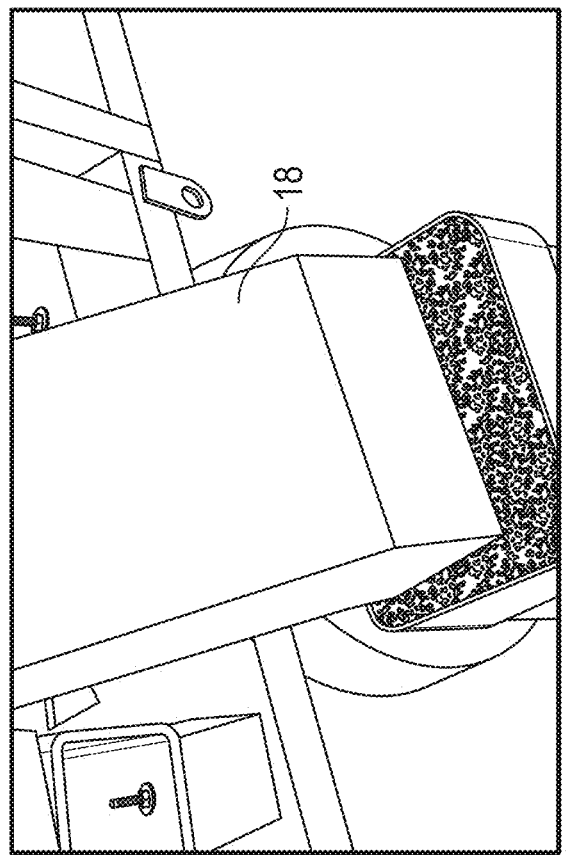
FIG. 21B is a perspective view of a portion of the exit chute of the waste-volume reduction system of FIG. 17.
Figure 21A:
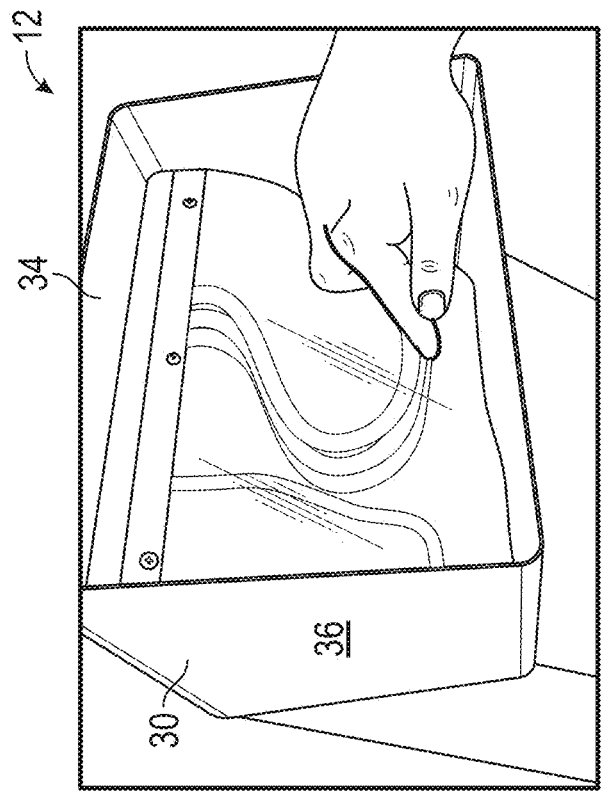
FIG. 21A is a perspective view of a portion of the feeder chute of the waste-volume reduction system of FIG. 17.

In some embodiments, the feeder chute 12 may have a length and may have one or more portions of the length having differing angles from one another, such as shown in FIGS. 2, 3 and 20. In some embodiments, the feeder chute 12 may have a length having at least two angles between portions of the length. In some embodiments, the length of the feeder chute 12 is configured such that a user cannot reach into the feeder chute 12 from the intake end 30 to reach the shredder assembly 16. Similarly, in some embodiments, there is not a direct line of sight from the intake end 30, through the feeder chute 12, to the inside of the shredder assembly 16. For example, the length of the feeder chute 12 may be configured to have one or more curvature along the length, such as a wave shape. Such a configuration prevents a user from reaching inside of the feeder chute 12 all the way to the shredder assembly 16, to prevent accidental contact of the user with the shredder assembly 16.

Figure 5:
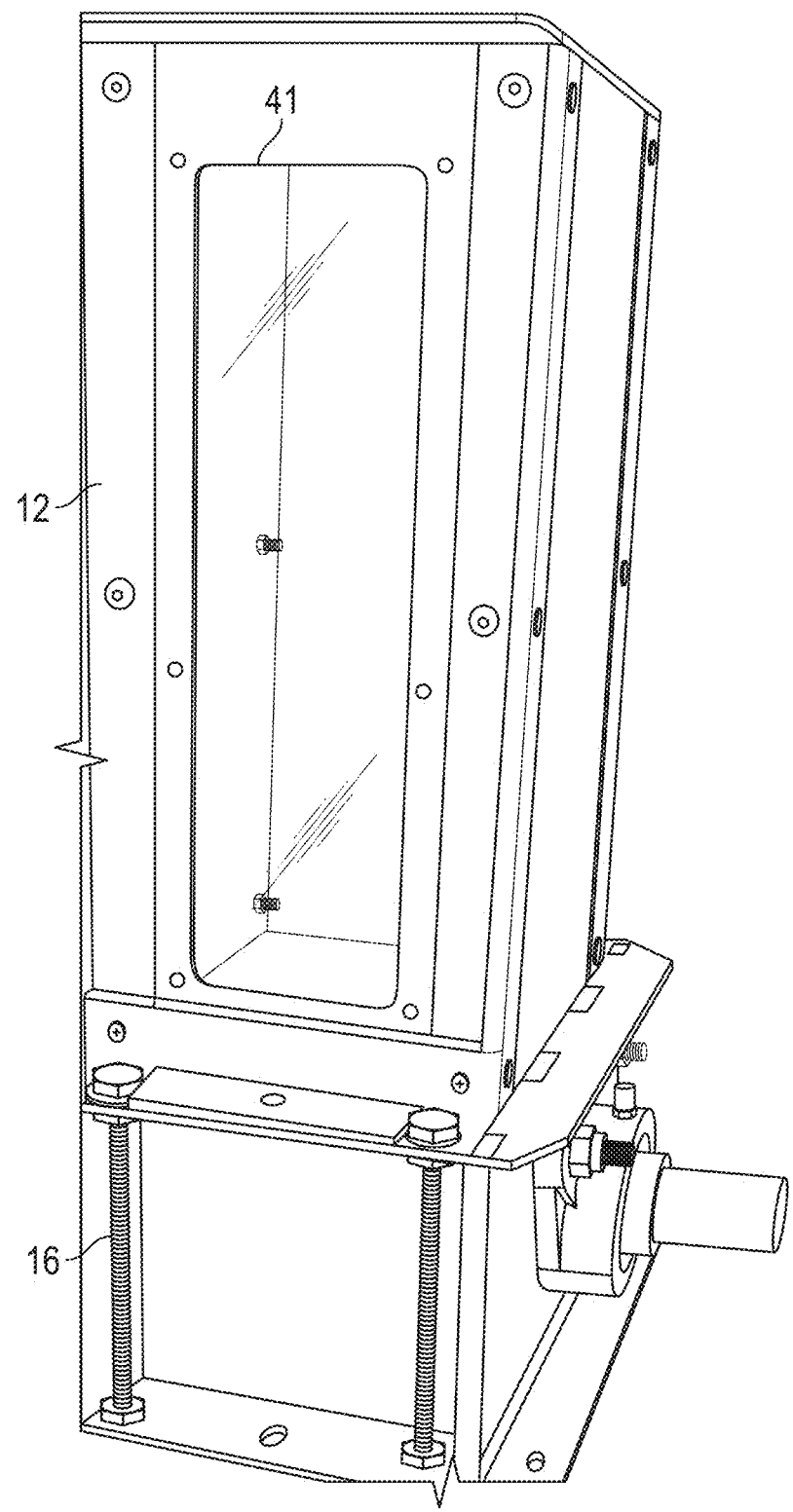
FIG. 5 is a perspective view of another exemplary feeder chute of the waste-volume reduction system in accordance with the present disclosure.

In some embodiments the feeder chute 12 may have one or more viewing window 41 and/or access door, such as shown in FIG. 5.

Figure 6:
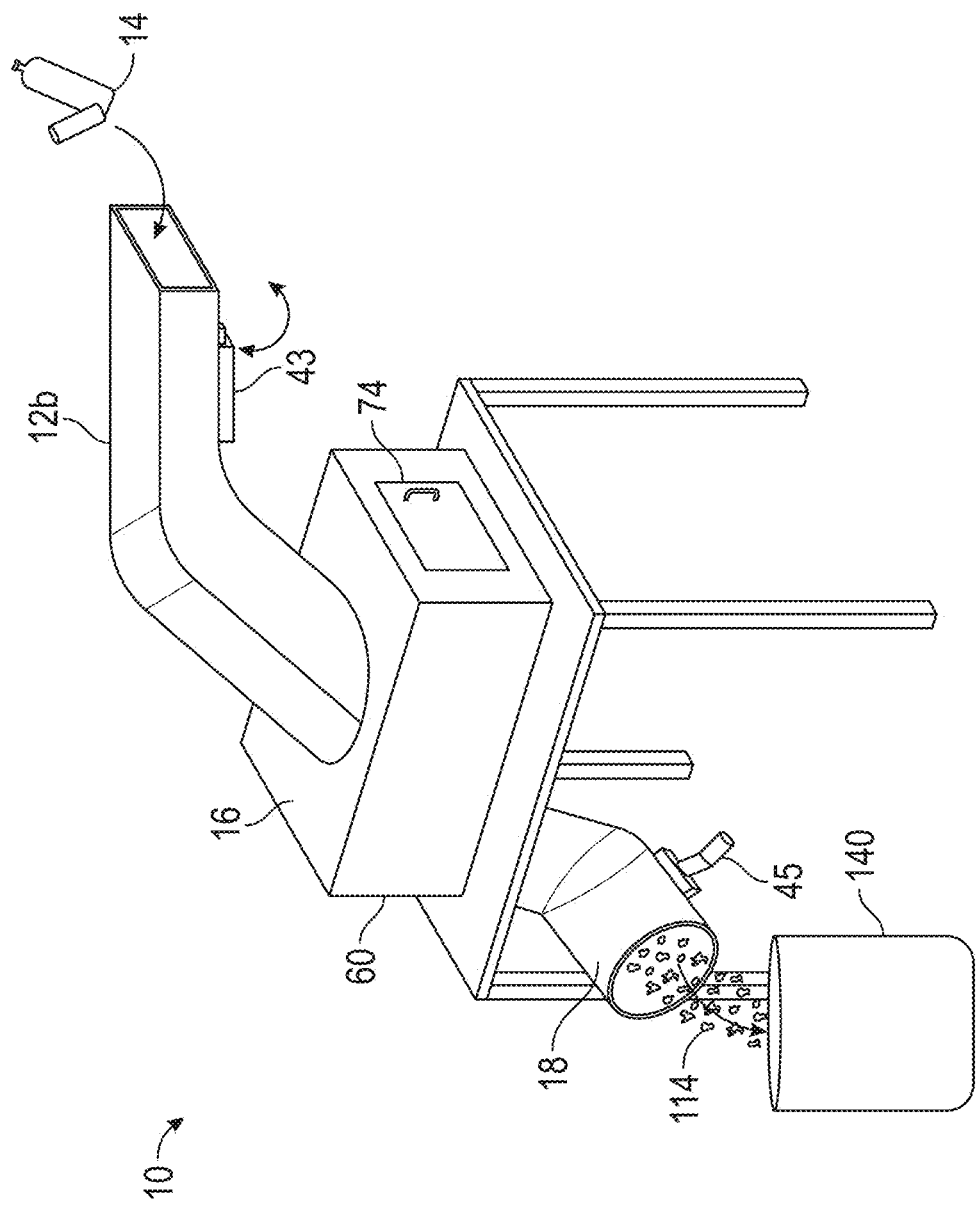
FIG. 6 is a perspective view of components of an exemplary waste-volume reduction system in accordance with the present disclosure.

In some embodiments, as shown in FIG. 6, the waste-volume reduction system 10 may include an exemplary sorting-feeder chute 12b, which may include one or more magnet 43. The magnet 43 may be configured and positioned to catch and/or eject from the feeder chute 12 certain types of the waste 14 that may contain ferrous metal.

For exemplary purposes herein, the feeder chute 12 and the exemplary feeder chute 12a and the sorting-feeder chute 12b may be used interchangeably.

Figure 7B:
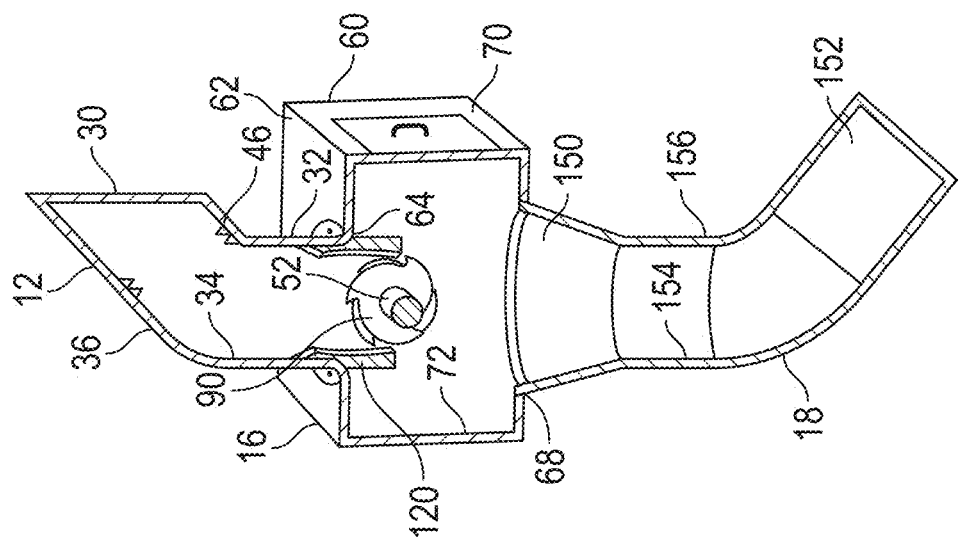
FIG. 7B is a cross-sectional view of the components of the waste-volume reduction system of FIG. 7A.
Figure 7A:
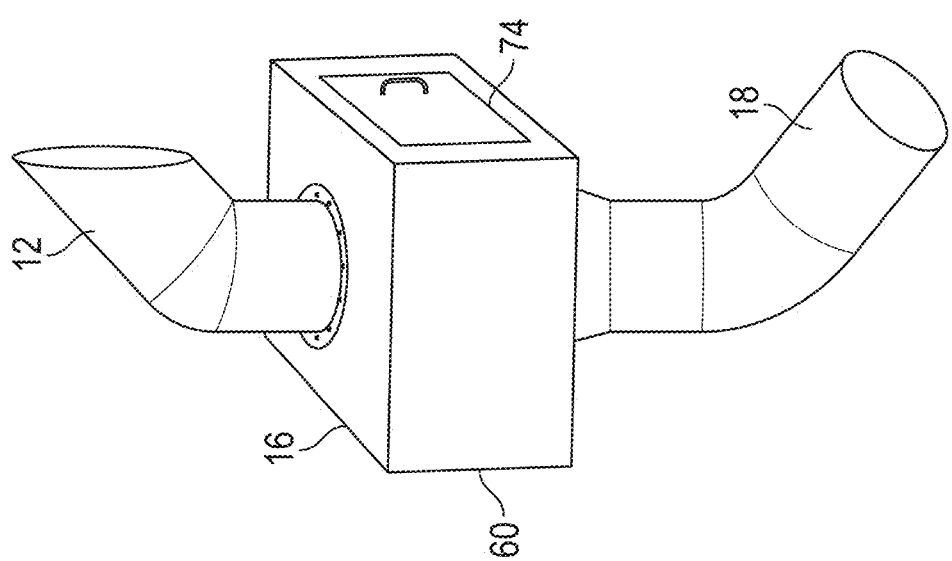
FIG. 7A is another perspective view of components of an exemplary waste-volume reduction system in accordance with the present disclosure.

As shown in FIG. 7A and FIG. 7B, in some embodiments, the waste-volume reduction system 10 may comprise one or more bag rippers 46 connected to the interior 34 of the feeder chute 12. The bag rippers 46 may comprise one or more blades, prongs, hooks, teeth, and/or other mechanism configured to catch and rip any exterior bags that may contain the waste 14 being ingested by the waste-volume reduction system 10. In some embodiments, the one or more bag rippers 46 in the interior 34 of the feeder chute 12 may be connected to one or more of the intake end 30, the output end 32, and between the intake end 30 and the output end 32 of the feeder chute 12.

As shown in FIGS. 1, 2, 11A, and 11B, the shredder assembly 16 may generally comprise a housing 60, a plurality of cleaning arms 120 attached to the housing 60, a shaft 52 within the housing 60, and a plurality of blades 90 attached to the shaft 52 within the housing 60. In some embodiments, the output end 32 of the feeder chute 12 may be attached to or integrated with the housing 60.

The housing 60, for example, as shown in FIG. 7A and 7B, has a length (L) and a width (w), a top 62 defining a first opening 64, a bottom 66 defining a second opening 68, and a wall 70 extending between the top 62 and the bottom 66, and cooperating with the top 62 and the bottom 66 to form an interior 72 of the housing 60. The first opening 64 of the top 62 may be positioned proximate to the output end 32 of the feeder chute 12 and aligned with at least a portion of the interior 34 of the feeder chute 12, so as to accept waste 14 from the feeder chute 12. In some embodiments, the top 62 of the housing 60 may also be the stationary plate 42 (FIG. 3). In other cases, the top 62 may be connected to the stationary plate 42 so as to connect the housing 60 to the feeder chute 12.

Figure 8:
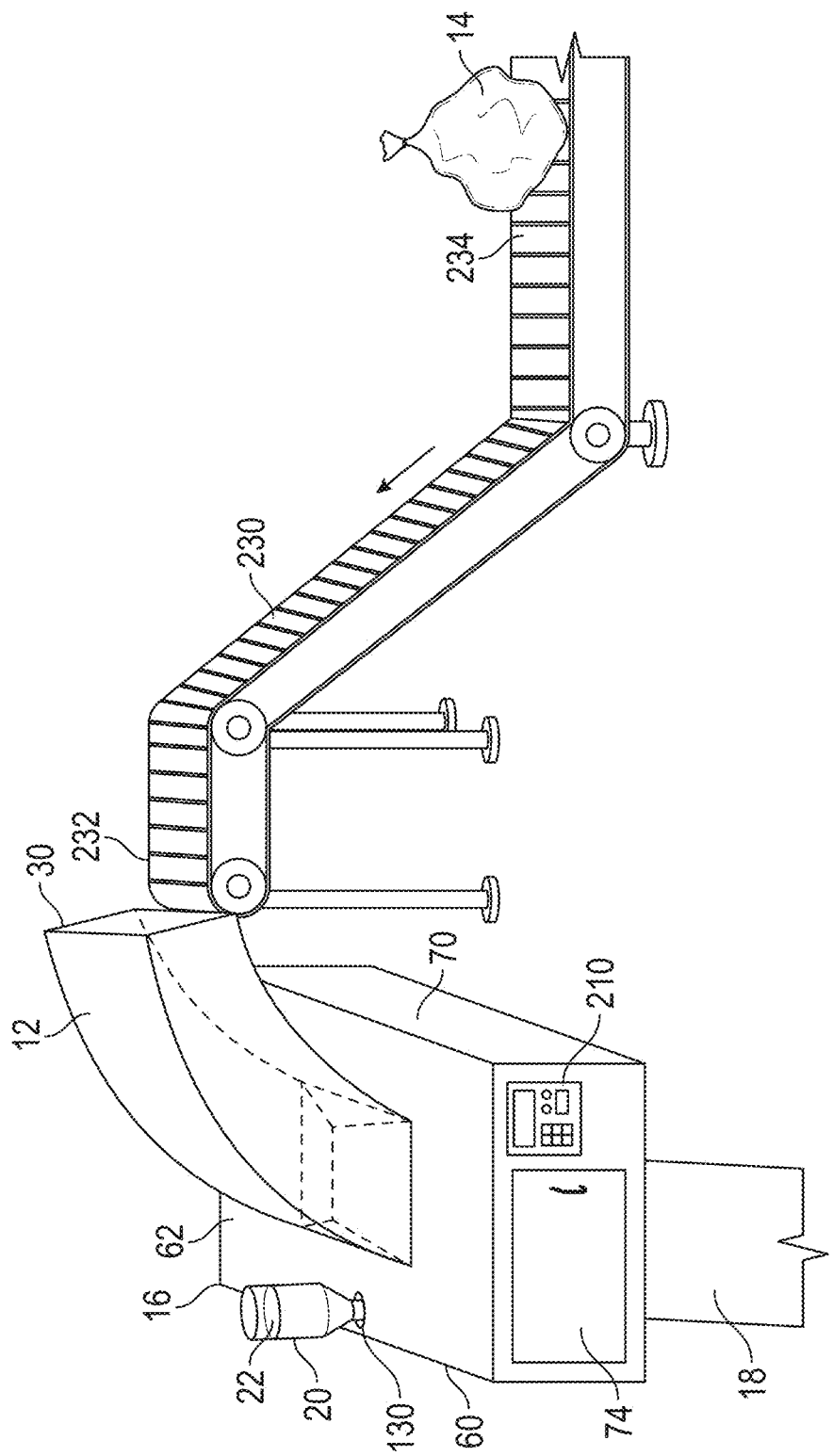
FIG. 8 is a top side perspective view of components of an exemplary waste-volume reduction system in accordance with the present disclosure.

In some embodiments, as shown in FIGS. 6-8, the housing 60 may have a door 74 that allows access into the interior of the housing 60. In some embodiments, one or more portions of the housing 60 may be configured to be removable to provide access into the interior 72 of the housing 60. In some embodiments, the top 62 may have an at least partially rounded shape (for example, as shown in FIGS. 1 and 2) and/or the top 62 may have a substantially flat shape (for example, as shown in FIGS. 7A and 7B).

It will also be understood that the waste-volume reduction system 10 may include one or more additional housing and/or that one or more components of the waste-volume reduction system 10 may share the housing 60 of the shredder assembly 16.

Figure 9:
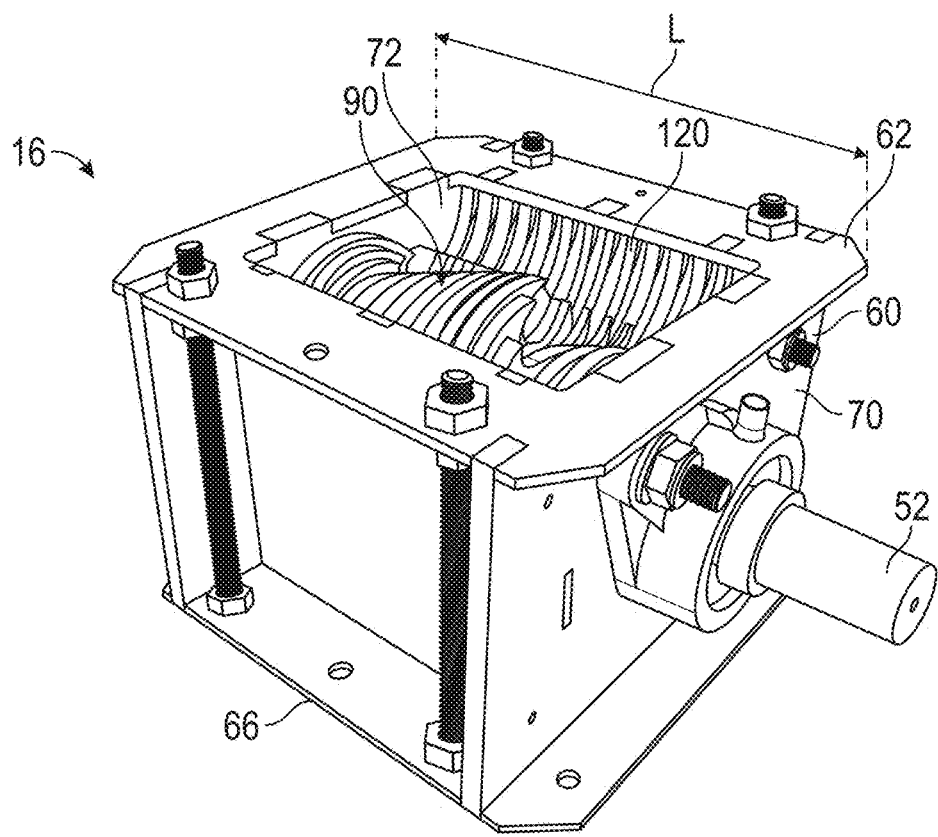
FIG. 9 is a top side perspective view of an exemplary shredder assembly in accordance with the present disclosure.
Figure 10:
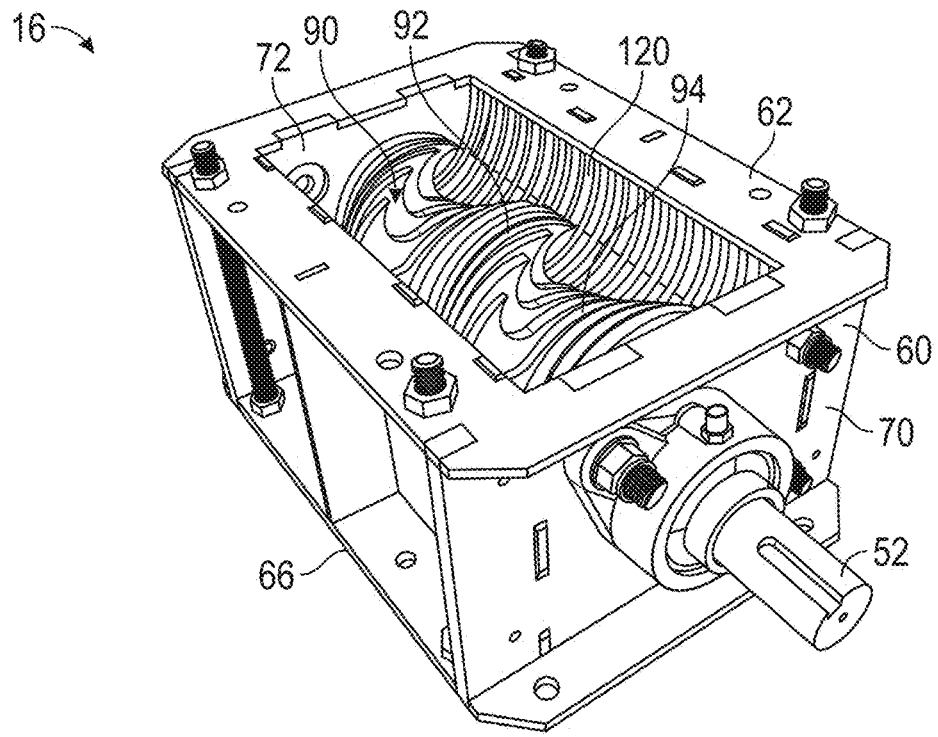
FIG. 10 is another top side perspective view of the exemplary shredder assembly of FIG. 9.

As shown in FIGS. 1 and 9-10, the shaft 52 of the shredder assembly 16 may extend within the housing 60 along the length (L) of the housing 60. The shaft 52 may be positioned between the top 62 and the bottom 66 of the housing 60. The shaft 52 is rotatable about a second axis 80. In some embodiments, optionally, the second axis 80 may be orthogonal to the first axis 40. The end of the shaft 52 may extend through the wall 70 of the housing 60, as illustrated in FIGS. 9 and 10.

In some embodiments, at least a portion of the shaft 52 of the shredder assembly 16 may have a cross section orthogonal to the second axis 80 that is polygonal shaped. In some embodiments, the cross section of the shaft 52 orthogonal to the second axis 80 may be hexagonal shaped.

As shown in FIGS. 9-12, the shredder assembly 16 may include the plurality of blades 90 about the shaft 52. The plurality of blades 90 may be configured and/or positioned so as to shred the waste 14 into shredded pieces 114 when the shaft 52 rotates thereby rotating the plurality of blades 90. The plurality of blades 90 may comprise at least a first blade 92 and a second blade 94. In some embodiments, the first blade 92 may be rotationally offset about the second axis 80 on the shaft 52 from the second blade 94. The first blade 92 may be longitudinally offset from the second blade 94. In some embodiments, the first blade 92 and the second blade 94 may have the same shape. In some embodiments, the first blade 92 and the second blade 94 may have different shapes from one another, such as shown in FIGS. 12A and 12B. In some embodiments, the first blade 92 may have two or more points and/or cutting edges. In some embodiments, the second blade 94 may have three or more points and/or cutting edges.

In some embodiments, one or more of the plurality of blades 90 of the shredder assembly 16 may have a complimentary polygonal opening 96 configured to accept the portion of the shaft 52 having a polygonal cross section. In some embodiments, and the polygonal opening 96 of one or more of the plurality of blades 90 is a hexagonal opening. The complimentary polygonal opening 96 is configured to transmit force to the shaft 52, which decreases the likelihood that the plurality of blades 90 may break away from the shaft 52.

Figure 13:
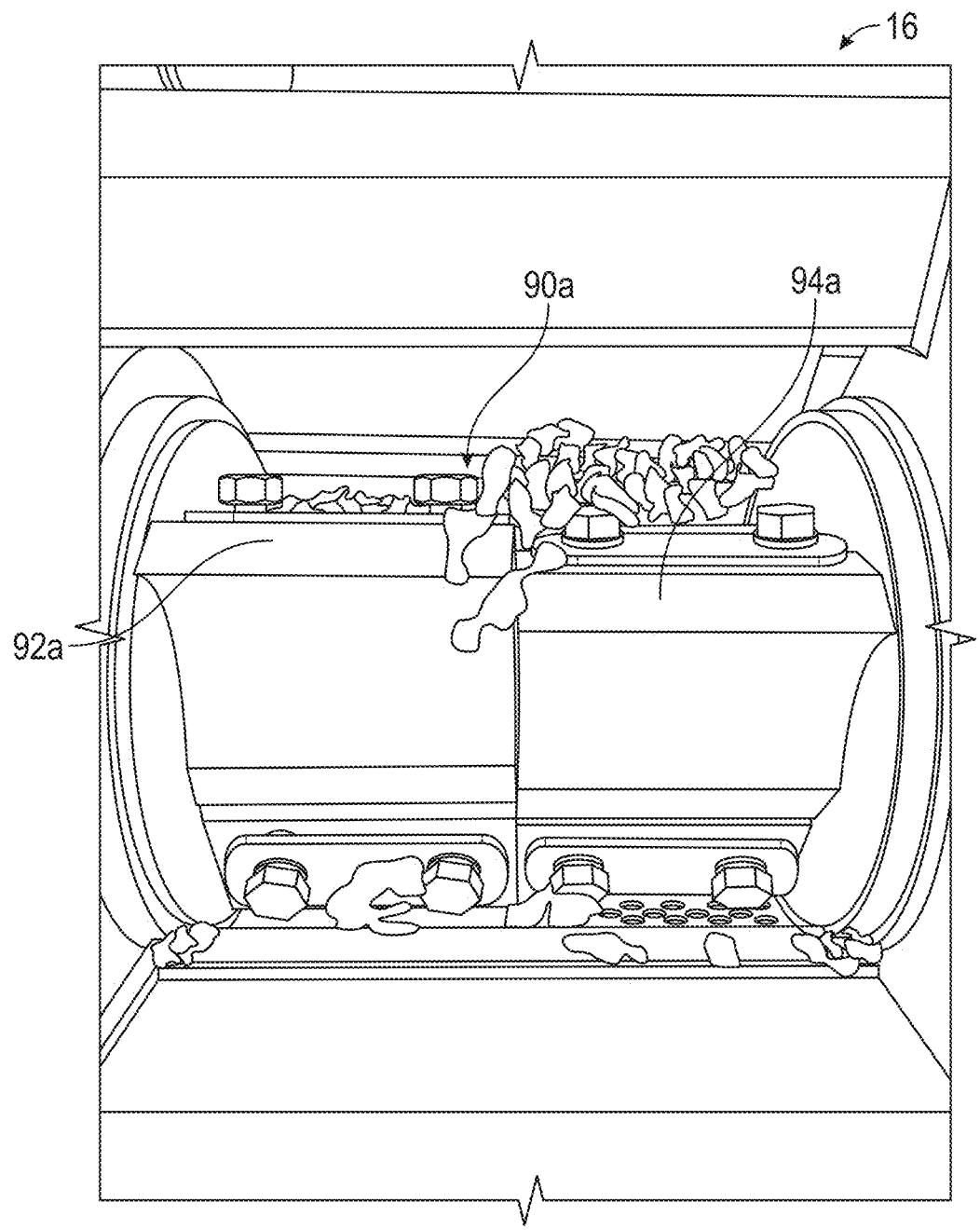
FIG. 13 is a side view of components of another exemplary shredder assembly in accordance with the present disclosure.

However, it will be understood that the plurality of blades 90 may have different shapes and sizes. For example, FIG. 13 illustrates another exemplary embodiment of a plurality of blades 90a in the shredder assembly 16, including a different first blade 92a and a different second blade 94a.

Figure 11A:
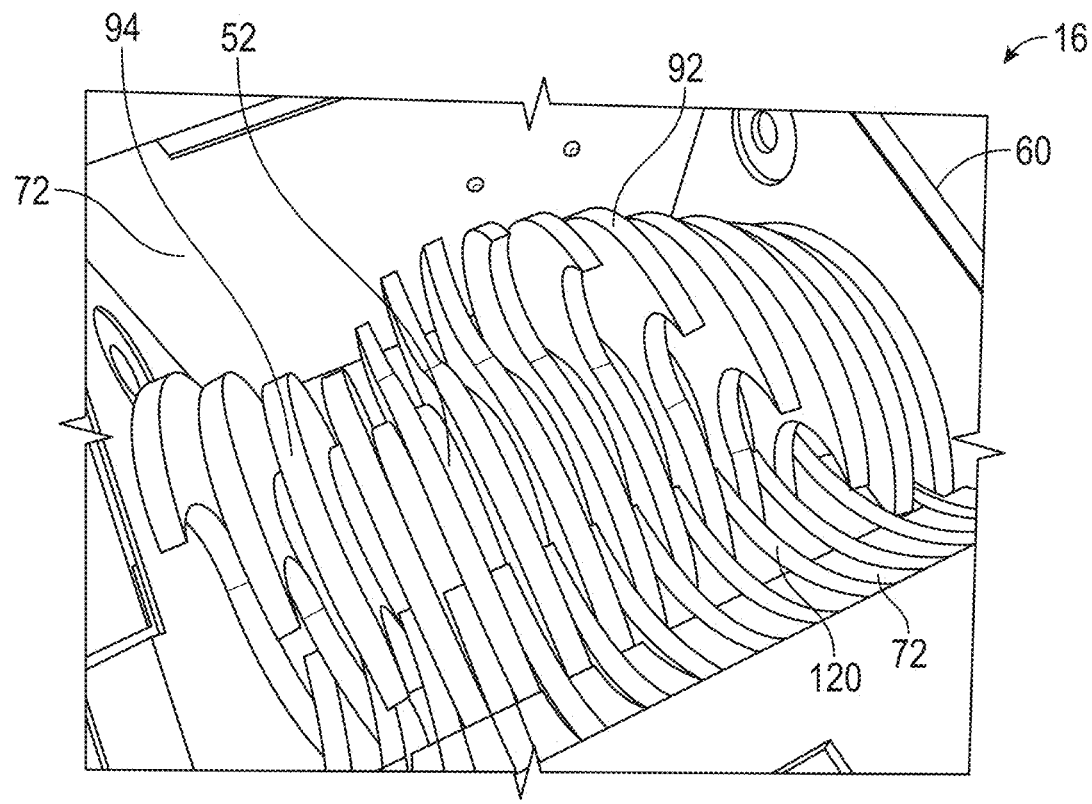
FIG. 11A is a top perspective view of components of the exemplary shredder assembly of FIGS. 9 and 10.
Figure 11B:
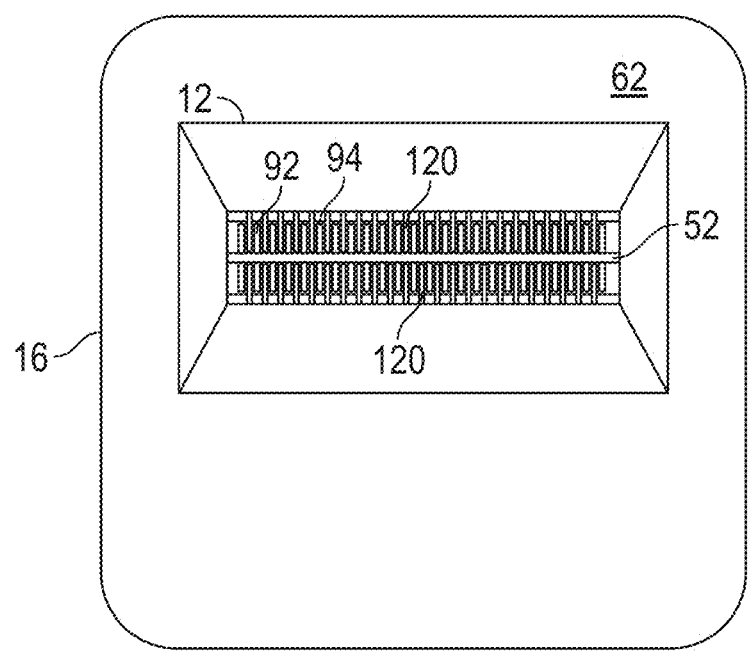
FIG. 11B is a top perspective view of components of another exemplary shredder assembly.
Figure 12B:
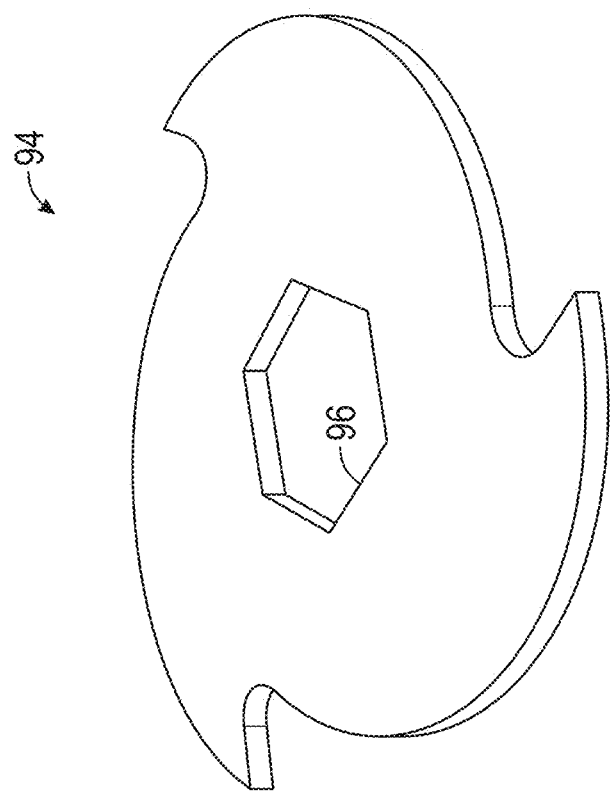
FIG. 12B is a perspective view of another exemplary shredder blade in accordance with the present disclosure.
Figure 12A:
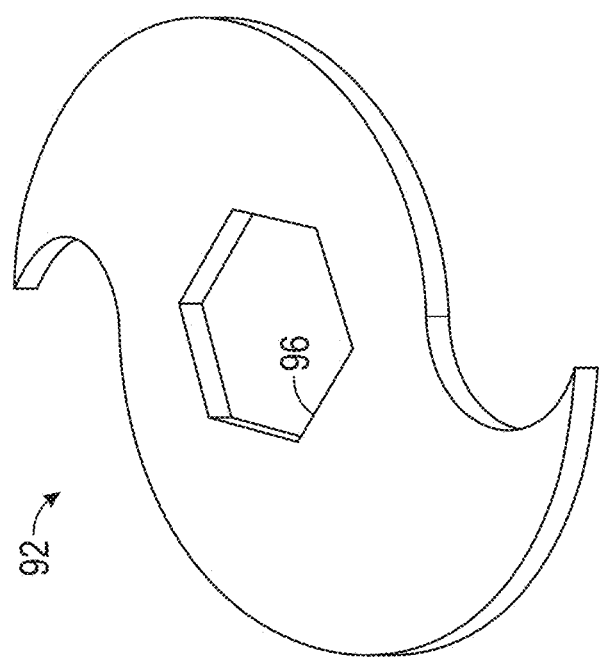
FIG. 12A is a top perspective view of an exemplary shredder blade in accordance with the present disclosure.

As shown in FIGS. 11A and 11B, the shredder assembly 16 may include a plurality of cleaning arms 120. The plurality of cleaning arms 120 may be attached within the interior 72 of the housing 60, such as to the wall 70 and/or the top 62 and/or the bottom 66 within the interior 72 of the housing 60. The plurality of cleaning arms 120 may be positioned such that at least a portion of one or more of the plurality of blades 90 passes between two or more of the cleaning arms 120 when the plurality of blades 90 is rotated within the housing 60 by the shaft 52. For example, in the example illustrated in FIG. 7B, the cleaning arms 120 are attached to the interior surface of the top 62 of the housing 60 and positioned such that the blades 90 pass through them without contact. As shown in this embodiment, and also the embodiment illustrated in FIG. 11B, the plurality of cleaning arms 120 may be attached to two sides of the wall 70 in the interior 72 on two sides of the plurality of blades 90. However, in other embodiments such as shown in FIGS. 9, 10, and 11A, the plurality of cleaning arms 120 may be attached to one side of the wall 70 in the interior 72 on one side of the plurality of blades 90.

The cleaning arms 120 may be any shape accordingly suited to the organization and shape of the blades 90 such that at least a portion of the blades 90 can pass between the cleaning arms 120 when rotating by the shaft 52, but does not contact the cleaning arms 120 when rotating. For example, the cleaning arms 120 may be shaped as regular or irregular prisms, such as a rectangular prism as shown in FIG. 7B. In other embodiments, the cleaning arms 120 may have one or more curved sides, such as those in FIG. 11, or may be cylindrical in shape. Further, the thickness of the cleaning arms 120 is similarly suited to accommodate the organization and shape of the blades 90 so that the blades 90 passing at least partially through the cleaning arms 120 when rotating by the shaft 52 do not contact the cleaning arms 120. For example, in one embodiment each of the cleaning arms 120 has a thickness of one quarter inch.

Further, the cleaning arms 120 may be configured to be removably engageable with the housing 60 so that the cleaning arms 120 can be repeatedly removed for cleaning and reattached, or be removed and replaced, or be adjusted. For example, the cleaning arms 120 may have one or more holes within at least one face of the cleaning arms 120 and one or more fasteners may engaging with the holes of the cleaning arms 120 to attach or remove the cleaning arms 120 from the housing 60 for cleaning, adjustment, or replacement.

Turning now to FIG. 8, in some embodiments, the additive reservoir 20 of the waste-volume reduction system may be positioned proximate to the shredder assembly 16. The additive reservoir 20 may be configured to contain one or more additives 22, such as one or more anti-microbial agents, anti-bacterial agents, and/or bacterial deterrent. The additive reservoir 20 may include, in some embodiments, an applicator 130. The additive reservoir 20 and/or applicator 130 may be attached to the system 10 during assembly or added later or replaced as needed.

The applicator 130 may be configured to dispense the additives 22. The applicator 130 may be configured to dispense the one or more additives 22 onto one or more of: the shredded pieces 114 of the waste 14, the plurality of blades 90, the interior of the feeder chute 12, the interior of the exit chute 18, and/or onto the waste 14 (such as when the waste enters or exits the feeder chute 12). The additive reservoir 20 may be configured to dispense the one or more additives 22 onto the cleaning arms 120 and/or blades 90 to clean the cleaning arms 120 and/or blades 90.

The applicator 130 may comprise one or more of a nozzle, a pump, a motor, and tubing. The applicator 130 may be gravity fed or may be computer controlled or may be mechanically controlled to dispense the one or more additives 22.

In some embodiments, the additives 22 may include one or more anti-microbial agents and/or anti-bacterial agents that may comprise one or more of a fluid anti-microbial agent, a solid anti-microbial agent, a fluid anti-bacterial agent, and a solid anti-bacterial agent. In some embodiments, the one or more anti-microbial agents and/or anti-bacterial agents may comprise one or more of antiseptics, antibiotics, antivirals, antifungals, antiparasitics, and disinfectants. In some embodiments, the one or more additives 22 may include one or more of agents having antimicrobial and antioxidant properties, for example, such as are used in packaging of food. In some embodiments, the one or more additives 22 may be configured to aid in processing solid food waste for anerobic digestion or bio-fuels.

In some embodiments, the additives 22 may comprise one or more of yeast and/or mixtures of enzymes to respond appropriately as needed to control waste. For example, adding yeast to the waste 14 (and/or shredded pieces 114 of the waste 14) when the waste 14 includes food or vegetation will help start the fermentation process, and mixtures of various enzymes will help start the digestive process for anaerobic digesters as well as certain composting factors. Anti-microbial agents and similar additives are safe and cellulosic contents of the waste 14 may be unaffected by the anti-microbial agents.

Returning again to FIG. 2, the exit chute 18 of the waste-volume reduction system 10 has an entry end 150 and an exit end 152. The exit chute 18 may have an interior surface 154 (FIG. 7B) and an exterior surface 156. In some embodiments, the entry end 150 may be aligned with the second opening 68 of the bottom 66 of the housing 60 of the shredder assembly 16, so as to accept the shredded pieces 114 of the waste 14 from the shredder assembly 16. In some cases, the entry end 150 may extend within the housing 60 through the second opening 68. The exit end 152 of the exit chute 18 is configured to dispense the shredded pieces 114 of the waste 14.

In some embodiments, as illustrated in FIG. 6, the exit chute 18 may include one or more intake fluid-bypass 45 positioned along the exit chute 18 and configured to drain fluid from the exit chute 18.

The exit end 152 of the exit chute 18 may be configured to accept a receiving bag 140 (FIGS. 6, 15A, 15B, 18 and 19). In some embodiments, the exit end 152 may be configured to accept the receiving bag 140 over the exterior surface 156 of the exit chute 18. In some embodiments, the exit end 152 may be configured to accept the receiving bag 140 within the interior surface 154 of the exit chute 18. In some embodiments, the exit chute 18 may be configured to output the shredded pieces of waste 14 into the receiving bag 140 whether or not the receiving bag 140 is in contact with the exit chute 18.

In some embodiments, the additives 22 may be previously applied to and/or dispensed by the applicator 130 into the one or more receiving bag 140 configured to receive the shredded pieces 114 of the waste 14.

Figure 14:
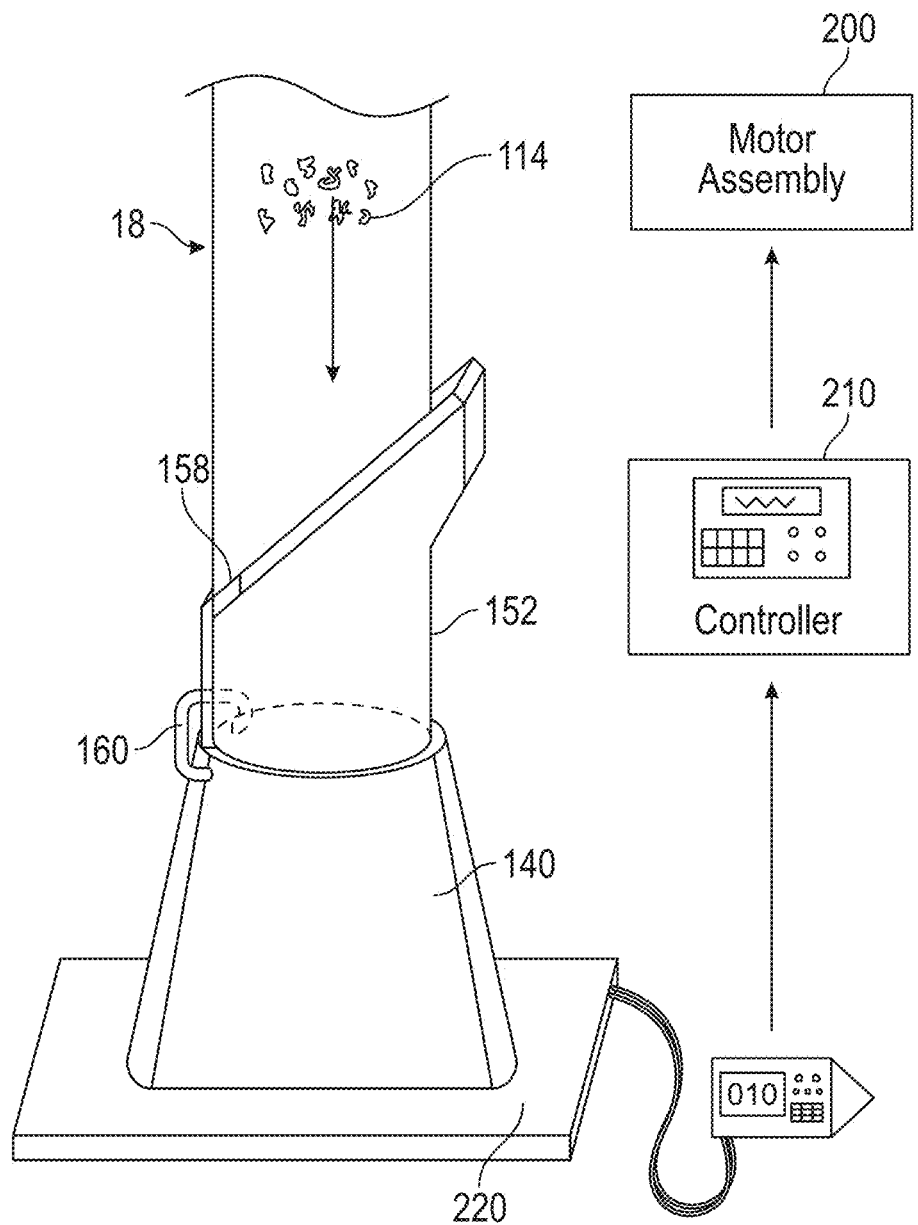
FIG. 14 is a perspective, partial schematic view of an exemplary exit chute and collection bag of the waste-volume reduction system in accordance with the present disclosure.

As shown in FIG. 14, in some embodiments, the exit chute 18 may have a shut-off 158 configured to close the exit chute 18 such that the shredded pieces 114 of the waste 14 does not exit the exit chute 18. In some embodiments, the shut-off 158 may be one or more of a valve, a lever, a door, and a flap.

Further shown in FIG. 14, in some embodiments, the exit chute 18 may have a catcher 160 extending from the exit chute 18 (such as from the interior surface 154 and/or the exterior surface 156) proximate to the exit end 152. The catcher 160 may be in the form of a hook or a prong, for example. The catcher 160 may be configured to catch a portion of the receiving bag 140 so as to seal the receiving bag 140 when the receiving bag 140 is removed from the exit chute 18.

As shown in FIGS. 15A and 15B, the receiving bag 140 has a top 170, a bottom 172, and one or more walls 174 extending between the top 170 and the bottom 172 of the receiving bag 140. The top 170, the bottom 172, and the one or more walls 174 may cooperate to create a waste-receiving interior with a bag opening 176. In some embodiments, the bag opening 176 may be configured to accept the exit end 152 of the exit chute 18. In some embodiments, the bag opening 176 may be configured to accept the shredded pieces 114 from the exit chute 18, whether or not the receiving bag 140 is attached to or surrounding the exit chute, such as when the receiving bag 140 is positioned proximate to the exit end 152 of the exit chute 18

The receiving bag 140 may be removable and may be configured to receive the shredded pieces 114 of the waste 14 through the bag opening 176. The receiving bag 140 may have a tab 178 extending into the bag opening 176 of the receiving bag 140. In some embodiments, the tab 178 covers an adhesive surface on a portion of the receiving bag 140, such that, when the receiving bag 140 is removed from the exit end 152 of the exit chute 18, the tab 178 is pulled away from the adhesive surface by the catcher 160 of the exit chute 18, thereby sealing the bag opening 176 of the receiving bag 140.

In some embodiments, the tab 178 may be configured to be pulled away from the adhesive surface by the catcher 160 when a predetermined weight is applied to (or within) the receiving bag 140, thereby pulling the receiving bag 140 away from the exit chute 18, engaging the tab 178 with the catcher 160, and pulling the receiving bag 140 closed.

The receiving bag 140 may be comprised of flexible material, such as one or more of flexible plastics, paper, cardboard, or other material, in some embodiments. In some embodiments, the receiving bag 140 may be a box or other container. In some embodiments, the receiving bag 140 is configured to stack with other receiving bags 140, once filled with the shredded pieces 114 of the waste 14.

Figure 16A:
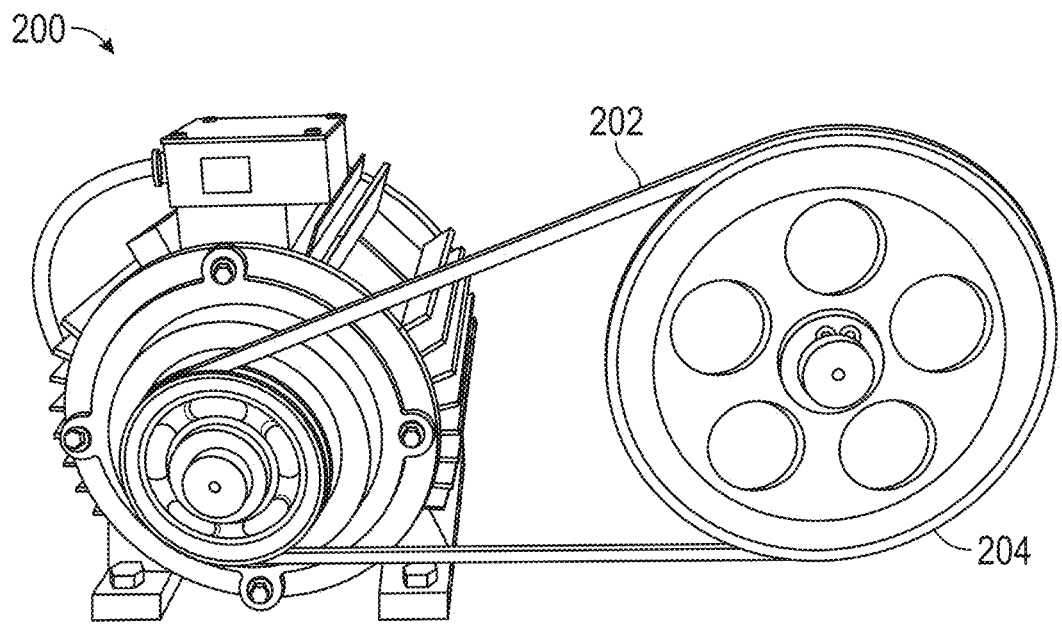
FIG. 16A is a perspective view of components of another exemplary waste-volume reduction system in accordance with the present disclosure.
Figure 16B:
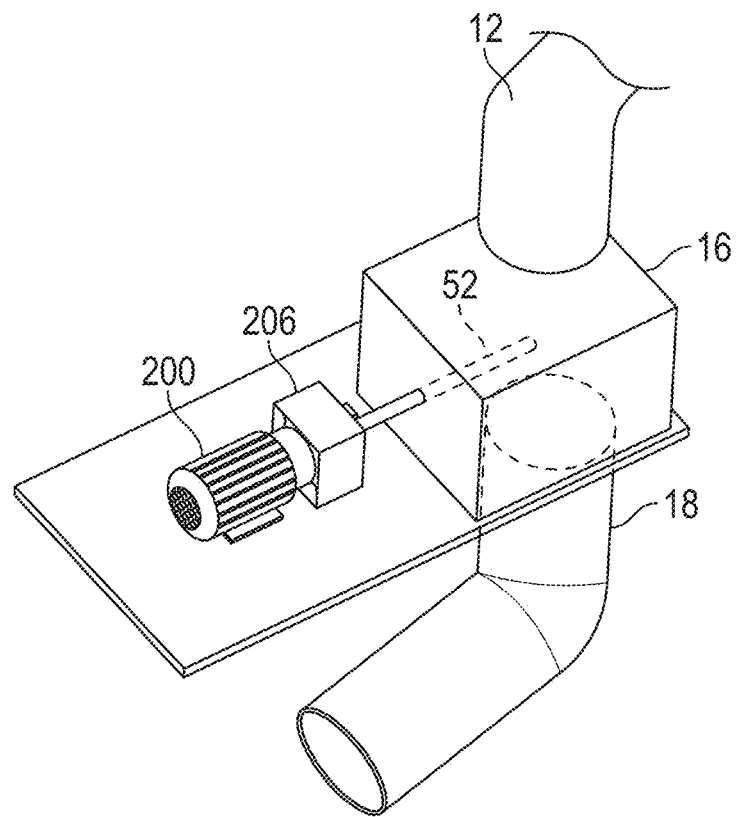
FIG. 16B is a perspective view of components of another exemplary waste-volume reduction system in accordance with the present disclosure.

As shown in FIGS. 1, 2, 16A, and 16B, in some embodiments, the waste-volume reduction system 10 may include, or may be connected to, a motor assembly 200. In some embodiments, the motor assembly 200 may be configured to drive and thereby rotate the input shaft 52. For example, the motor assembly may use one or more belts 202, drive wheels 204, and/or gears 206 to drive the input shaft 52. For example, as illustrated in FIG. 16B, the shaft 52 may be driven by the motor assembly 200 and the gears 206 in a gear box. The gears 206 may be configured to adjust power levels coming from the motor assembly 200 to the input shaft 52. However, it will be understood that the input shaft 52 may be driven in other ways, such as are well-known in the art.

Figure 17:
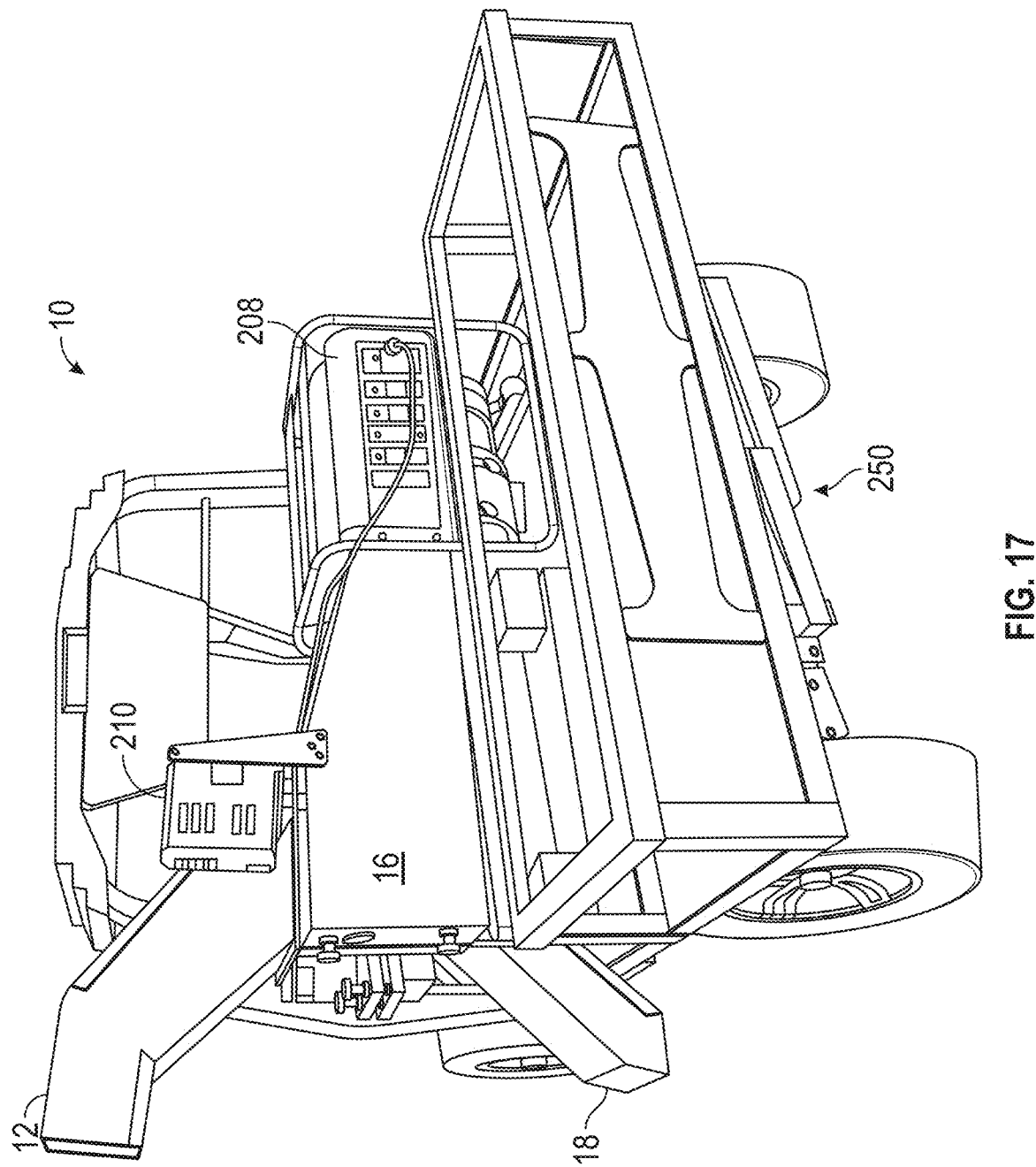
FIG. 17 is a perspective view of another exemplary waste-volume reduction system mounted on a vehicle in accordance with the present disclosure.
Figure 18:
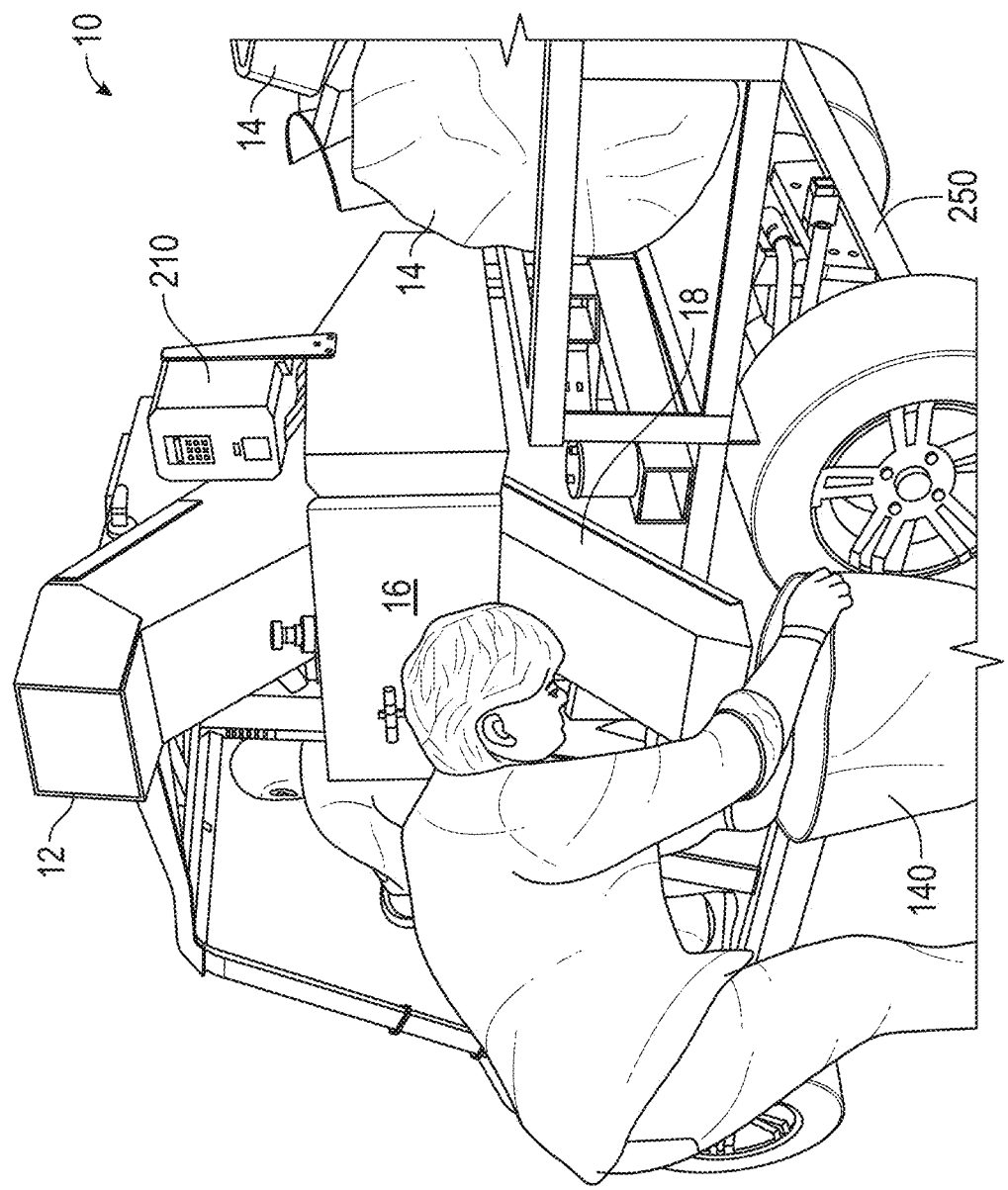
FIG. 18 is a perspective view the waste-volume reduction system of FIG. 17 in use.
Figure 19:
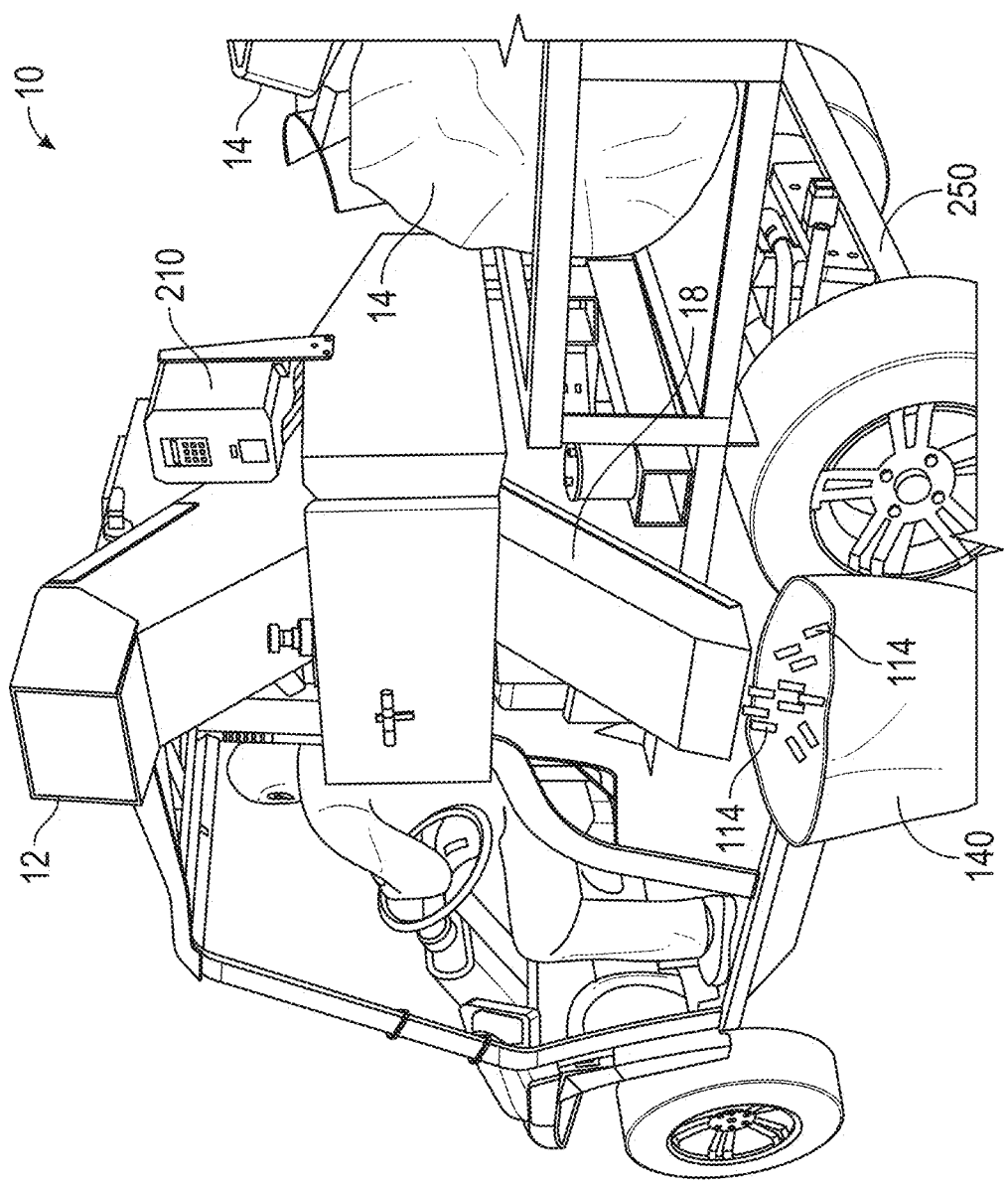
FIG. 19 is a perspective view the waste-volume reduction system of FIG. 17 in use.

In some embodiments, the waste-volume reduction system 10 may include, or may be connected to, a power source 208, such as a generator (FIG. 17) or a power grid. In some embodiments, the power source 208 may be a renewable energy system, such as solar power, wind power, or steam power.

As shown in FIG. 8, in some embodiments, the waste-volume reduction system 10 may include, or may be connected to, a controller 210. The controller may comprise one or more of: an on/off switch, circuitry, a computer processor, non-transitory computer memory configured to run one or more software applications, an input interface, an output interface, and a timer. The input interface may be configured to accept control inputs from a user. The output interface may be configured to output information to a user, such as via a visual or audio display.

In some embodiments, the controller 210 may be configured to change the motor assembly 200 from an active state to a passive state, as illustrated in FIG. 14. Optionally, the waste-volume reduction system 10 may include, or may be connected to, a scale 220 positioned proximate to the exit end 152 of the exit chute 18. The controller 210 may be in communication with the motor assembly 200 and the scale 220 such that the controller 210 may change the motor assembly 200 from an active state to a passive state when the controller 210 determines that the scale 220 detects a presence of a predetermined amount of weight on the scale 220 from the shredded pieces 114 of the waste 14.

In some embodiments, the controller 210 or a plurality of controllers 210 may be configured to implement artificial intelligence algorithms, and/or to receive instructions based on artificial intelligence algorithms.

In some embodiments, the waste-volume reduction system 10 may utilize artificial intelligence systems to identify various types of material(s) input into the waste-volume reduction systems 10. Utilizing art-disclosed computer vision solutions, artificial intelligence may be used to identify and/or differentiate the waste 14 made of plastics and the waste 14 made of aluminum cans. In another hypothetical example, artificial intelligence may be used to identify and/or differentiate a turtle from a plastic bag or bottle, and/or to control the waste-volume reduction system 10 to not pick up and/or process the turtle. In some embodiments, the waste-volume reduction system 10 may utilize artificial intelligence systems to control all or some functions of the waste-volume reduction system 10. For example, artificial intelligence systems may monitor and/or control debris weight, component mechanics, and component maintenance status.

In some embodiments, the waste-volume reduction system 10 may utilize artificial intelligence systems to navigate a moving version of the waste-volume reduction system 10 and/or a vehicle upon which the waste-volume reduction system 10 is mounted.

In some embodiments, there may be a plurality of the waste-volume reduction systems 10 and the controller 210 may be configured to communicate with and/or receive instructions from other controllers 210 in the plurality of the waste-volume reduction systems 10. In one non-exclusive hypothetical example, a first waste-volume reduction system 10 may be at a first location and a second waste-volume reduction system 10 may be at a second location, different than the first location. A first controller 210 for the first waste-volume reduction system 10 may communicate with a second controller 210 for the second waste-volume reduction system 10. In one embodiment, the first and second controllers 210 may communicate information regarding the operation of the first and second waste-volume reduction systems 10, such as how much waste 14 has been processed, a weight of the waste 14 and/or the shredded pieces 114 of the waste 14, an amount of run time, and so on. In some embodiments, a central processor (and/or central controller 210) may compile such information and output such information to a user, such as waste reduction, costs etc.

In some embodiments, the plurality of waste-volume reduction systems 10 may have a central controller 210 that is configured to control multiple ones of the waste-volume reduction systems 10 and/or to receive information from multiple ones of the waste-volume reduction systems 10. In some embodiments, one or more of the controllers 210 may be in the cloud.

In some embodiments, the controller 210 may be remotely located from the waste-volume control system 10. In some embodiments, the controller 210 may be a drone or a handheld device. In one example, a user may utilize a remotely located controller 210 to drive a mobile version of the waste-volume reduction system 10, such as while walking beside the waste-volume reduction system 10, or from a distance from the waste-volume reduction system 10.

In some embodiments, the waste-volume control system 10 may include and/or be connected to a remote software application (an "app") that may be run on the cloud or one or more remote processor. In one hypothetical example, the remote software application may receive information from the waste-volume control system 10, such as performance metric information and/or status information (e.g., how much fuel remains, tire pressure, health check of the system, etc.).

In some embodiments, a software application may be used to monitor a plurality of the waste-volume control systems 10. In a hypothetical example, the software application may be run on a smart device (such as a tablet or smartphone or other processor device) and may display the status of one or more of the plurality of the waste-volume control systems 10, such as which unit needs attention (e.g., Unit 3 is 50% full so it will need a bag change). This is an improvement over current systems that require manual checks to change bags on trash cans that are overflowing.

As shown in FIG. 8, optionally, in some embodiments, the waste-volume reduction system 10 may include, or may be connected to, a conveyor 230 having a first end 232 and a second end 234, the first end 232 positioned proximate to the intake end 30 of the feeder chute 12 so as to channel the waste 14 into the intake end 30 of the feeder chute 12. In some embodiments, the conveyor 230 may include or be attached to a mechanism for picking up the waste 14.

Further, in some embodiments, the waste-volume reduction system 10 may be mobile. For example, as shown in FIGS. 1 and 2, the waste-volume reduction system 10 may include one or more wheels 240 to mobilize the system 10 and/or any components of the system 10. The waste-volume reduction system 10 may be mobile via manual force, remote operation, or it may be self-driven to move and gather waste 14.

As shown in FIGS. 17-21, in some embodiments, the waste-volume reduction system 10 may be configured to be mountable to a vehicle 250. Nonexclusive examples of mounting configurations include the use of one or more of adjustable railings, fixed welding, bolted into a platform, fixated onto sliders, D-rings or other type hooks, and secured inside a solid or adjustable frame. For example, the waste-volume reduction system 10 may be configured to be mountable on rails on a bed of a vehicle 250 such that the waste-volume reduction system 10 may be moved on the rails and locked down to the rails.

In some embodiments, the waste-volume reduction system 10 may be part of a disaster rig configured to be moveable to scenes of disaster for waste-volume reduction on site.

Figure 22:
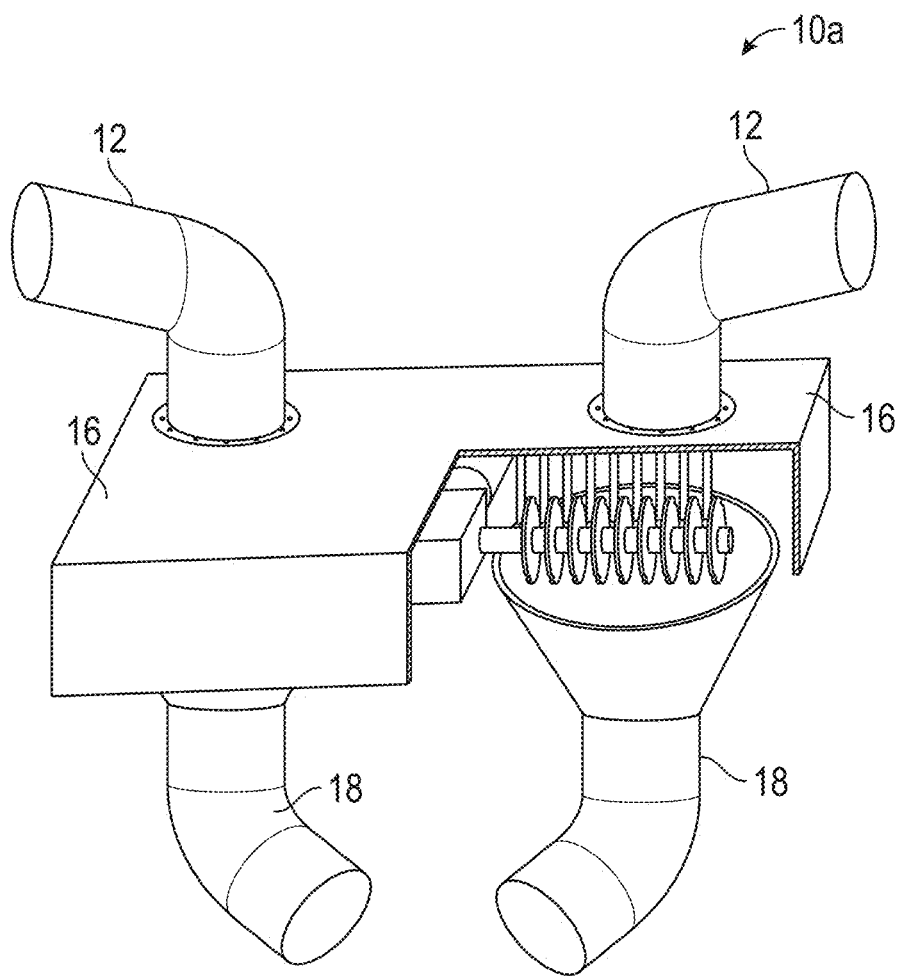
FIG. 22 is a perspective view of another exemplary waste-volume reduction system with a partial cutaway in accordance with the present disclosure.

Turning now to FIG. 22, shown therein is another embodiment of a waste-volume reduction system 10a, which is similar to the waste-volume reduction system 10 previously described, but which may have two or more feeder chutes 12 and two or more shredder assemblies 16. In some embodiments, the two or more shredder assemblies 16 include a first shredder assembly 16 having a first plurality of blades 90 and a second shredder assembly 16 having a second plurality of blades 90. In some embodiments, the first plurality of blades 90 may be configured to shred a first type of the waste 14 and the second plurality of blades 90 may be configured to shred a second type of the waste 14 different than the first type of the waste 14. The first type of the waste 14 and the second type of the waste 14 may include one or more of metal, plastic, food, cardboard, paper, mixed-media, diapers, vegetation, wood, and other waste. In some embodiments, the first shredder assembly 16 and the second shredder assembly 16 may work independently from one another, such that one of the first shredder assembly 16 and the second shredder assembly 16 is active while the other is passive, or may work at different rates of speed. In some embodiments, the first shredder assembly 16 and the second shredder assembly 16 may work consecutively. In some embodiments, the waste-volume reduction system 10a may have one exit chute 18. In other cases, the system 10a may have or two or more exit chutes 18, as illustrated in FIG. 22.

Figure 23:
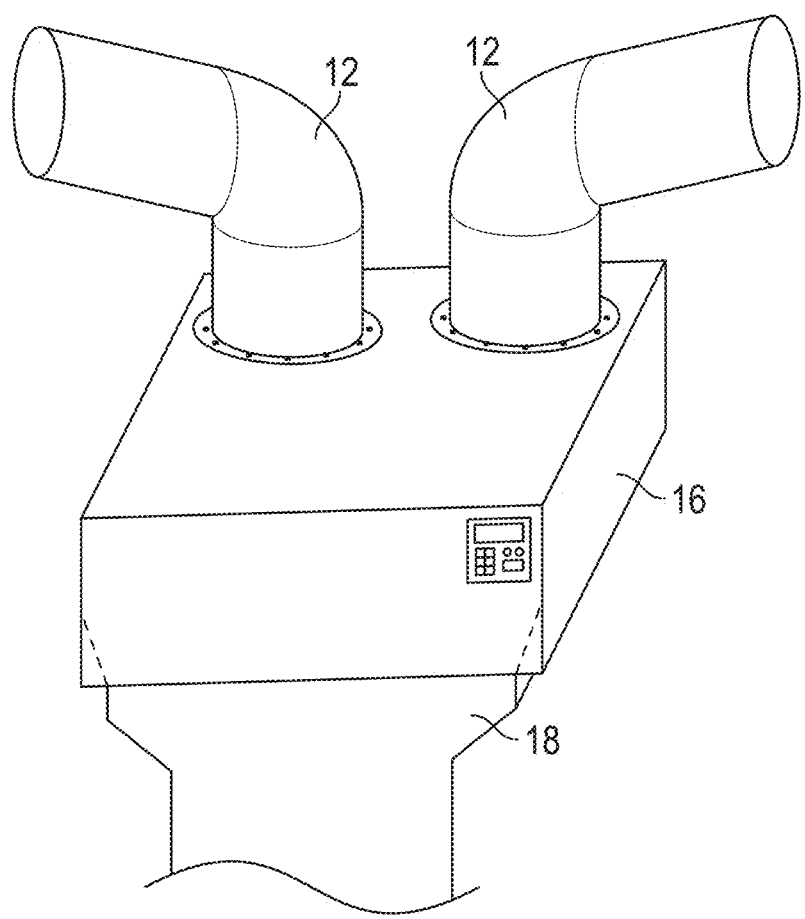
FIG. 23 is a perspective view of yet another exemplary waste-volume reduction system in accordance with the present disclosure.
Figure 24:
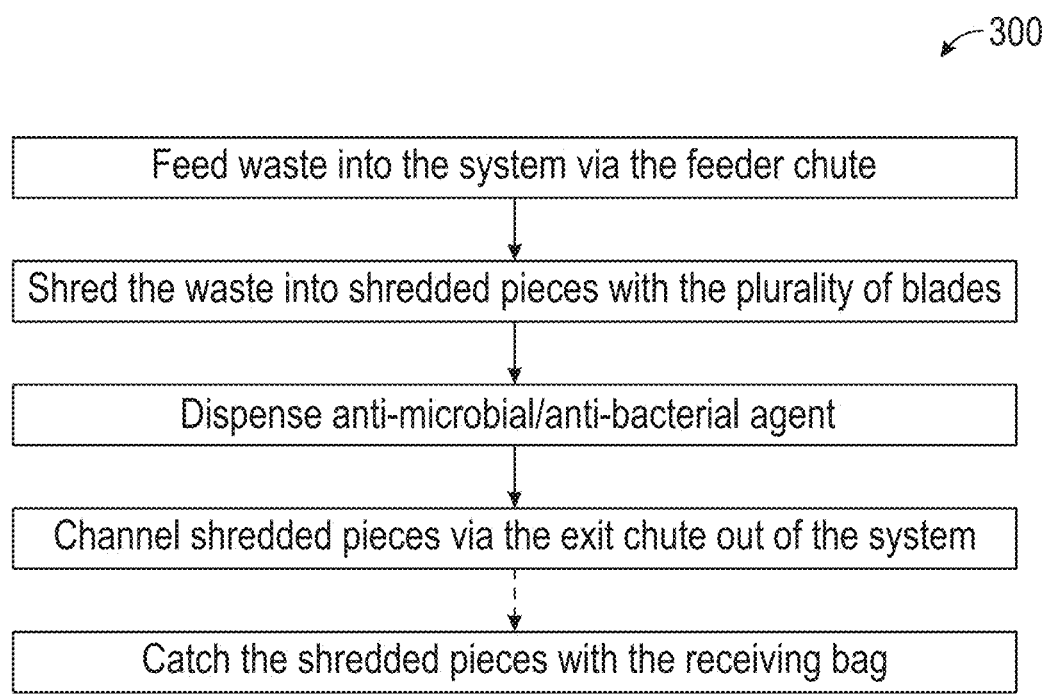
FIG. 24 is a process flow diagram of an exemplary method of use of a waste-volume reduction system in accordance with the present disclosure.

Turning now to FIG. 23, shown therein is another embodiment of a waste-volume reduction system 10b, which is similar to the waste-volume reduction system 10 previously described, but which may have two or more feeder chutes 12 that feed the waste 14 into a common shredder assembly 16. The waste-volume reduction system 10b may have one or more exit chutes 18 as well.

Figure 29:
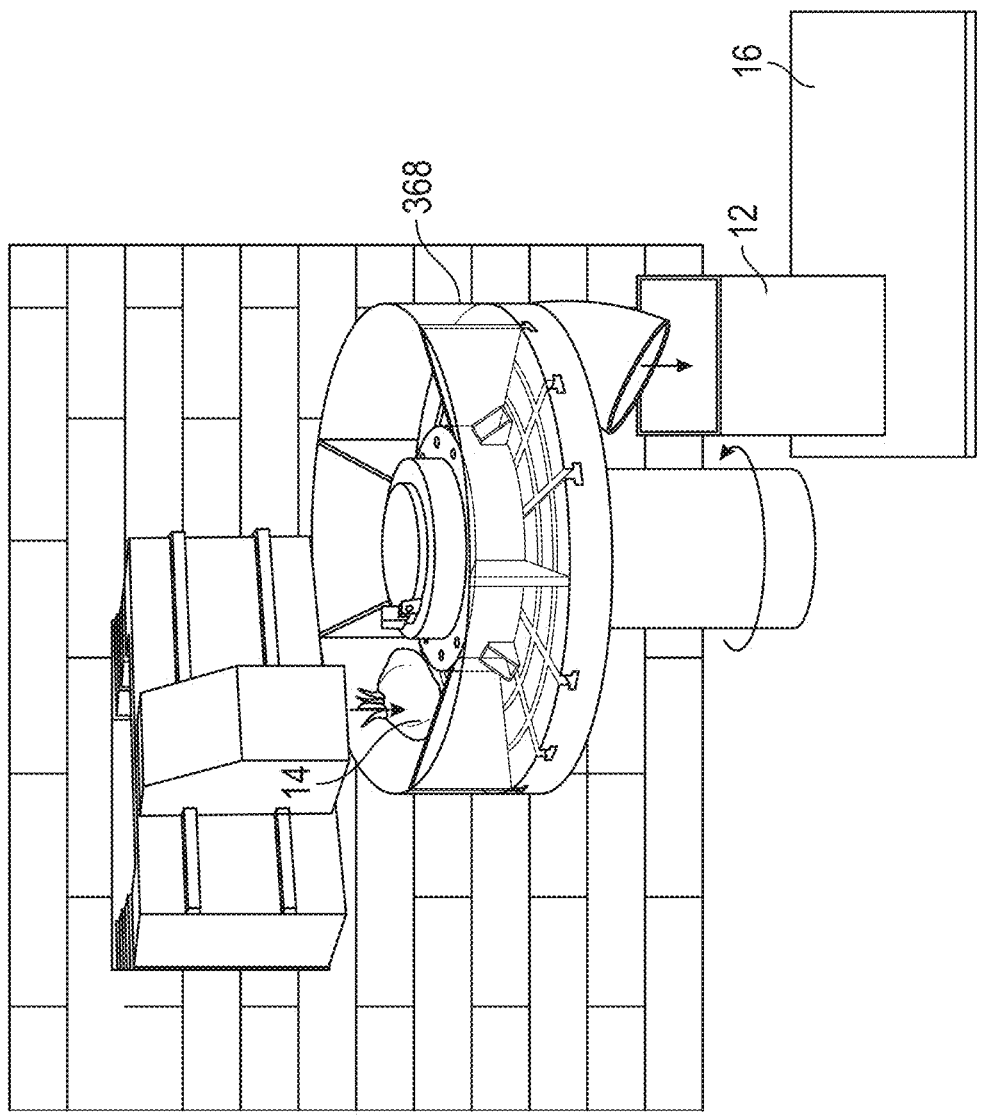
FIG. 29 is a perspective view of yet another exemplary waste-volume reduction system in accordance with the present disclosure.

Methods of use of the waste-volume reduction system 10 for waste-volume reduction will now be described. In one embodiment, as illustrated in FIG. 29, a method of waste-volume reduction method 300 may comprise feeding the waste 14 into the feeder chute 12 through the intake end 30 into the interior 34 of the feeder chute, which is then output out of the output end 32, thereby channeling the waste 14 through the feeder chute 12 into the shredder assembly 16. The method may further comprise shredding the waste 14 into the shredded pieces 114 of the waste 14 with the shredder assembly 16, by feeding the waste 14 through the first opening 64 of the top 62 of the housing 60 into the plurality of blades 90 rotated by the shaft 52, the plurality of blades 90 cleaned by the plurality of cleaning arms 120 attached to the interior 72 of the housing 60 positioned such that at least a portion of one or more of the plurality of blades 90 passes between two or more of the cleaning arms 120 when the plurality of blades 90 is rotated within the housing 60 by the shaft 52.

The method 300 may comprise dispersing one or more additives 22 (such as anti-microbial agents and/or anti-bacterial agents) from the additive reservoir 20, which may be positioned proximate to the shredder assembly 16.

The method 300 may comprise channeling the shredded pieces 114 of the waste 14 from the shredder assembly through the entry end 150 of the exit chute 18 and out of the exit end 152 of the exit chute 18. Optionally, in some embodiments, the method 300 may comprise catching the shredded pieces 114 of the waste 14 in one or more of the receiving bags 140.

The shaft 52 of the shredder assembly 16 may be rotated with the motor assembly 200.

The conveyor 230 may be utilized to channel the waste 14 into the intake end 30 of the feeder chute 12.

In some embodiments, the method 300 may include placing the receiving bag 140 proximate to the exit end 152 of the exit chute 18 and removing the receiving bag 140 when the receiving bag 140 receives a predetermined amount of the shredded pieces 114 of the waste 14. In some embodiments, removing the receiving bag 140 includes catching the tab 178 with the catcher 160 of the exit chute 18, thereby exposing the adhesive surface and then sealing the bag opening 176 of the receiving bag 140.

In some embodiments, the method 300 further comprises changing, with the controller 210 in communication with the motor assembly 200, the motor assembly 200 from an active state to a passive state. In some embodiments, the method 300 further comprises changing, with the controller 210 in communication with the motor assembly 200, the motor assembly 200 from an active state to a passive state when a scale 220, positioned proximate to the exit end 152 of the exit chute 18 (and/or under the receiving bag 140), detects a presence of a predetermined amount of weight on the scale 220.

Figure 25:
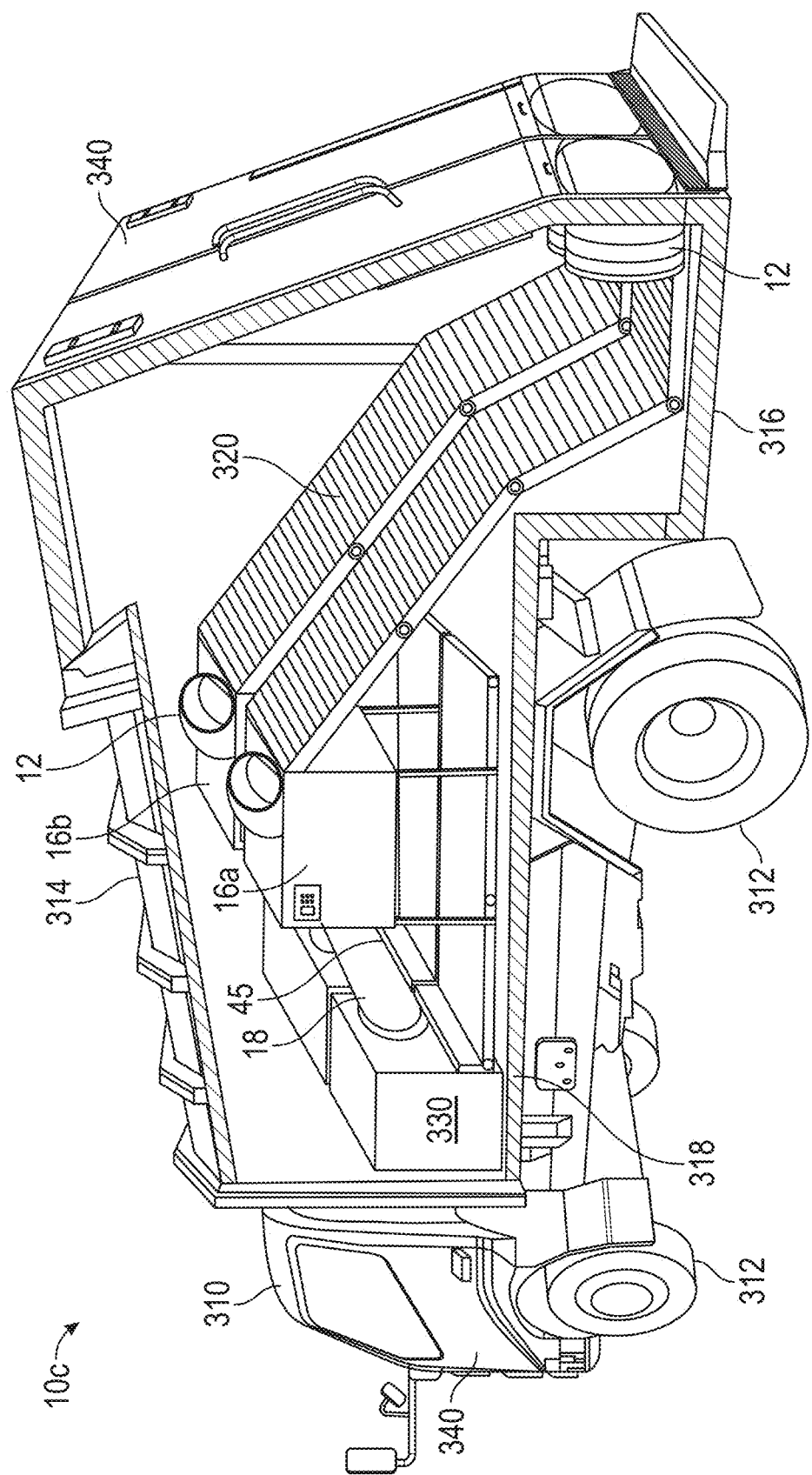
FIG. 25 is a perspective partial cross-sectional view of an exemplary waste-volume reduction rig system in accordance with the present disclosure.

Turning now to FIG. 25, shown therein is an exemplary embodiment of a waste-volume reduction rig system 10c, which is similar to the waste-volume reduction system 10, excepted as described. The waste-volume reduction rig system 10c may include a transporter 310. Nonexclusive examples of the transporter 310 include a box truck, tractor trailer, or other means of transport. The transporter 310 may have one or more transporter wheels 312. The transporter 310 may have a top 314, a bottom 316, and/or one or more sides 318.

The waste-volume reduction rig system 10c may include one shredder assembly 16 or a plurality of the shredder assemblies 16. In some embodiments, the plurality of shredder assemblies 16 may be from two to ten shredder assemblies 16. In some embodiments, the plurality of shredder assemblies 16 may be staggered with rollers and/or may have varying sizes of blades 90. One or more of the plurality of shredder assemblies 16 may be separately connected to corresponding motor assemblies 200 and/or power sources or may share one or more motor assemblies 200 and/or power sources.

Figure 25A:
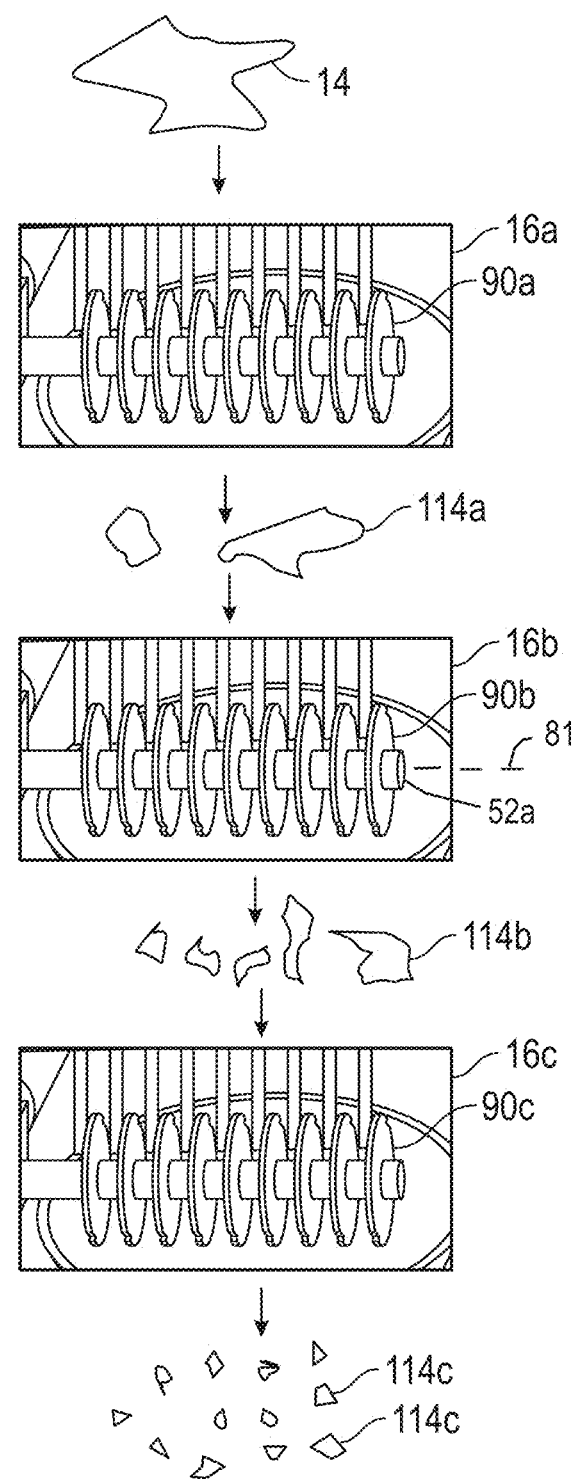
FIG. 25A is a schematic view of a plurality of exemplary shredder assemblies in accordance with the present disclosure.

In some embodiments, such as shown in FIG. 25A the plurality of the shredder assemblies 16 may include a first shredder assembly 16a having a first plurality of blades 90a, a second shredder assembly 16b having a second plurality of blades 90b, and a third shredder assembly 16c having a third plurality of blades 90c. In some embodiments, the first plurality of blades 90a may be configured and/or spaced to shred the waste 14 into first shredded pieces 114a having a first size, the second plurality of blades 90b may be configured and/or spaced to shred the first shredded pieces 114a into second shredded pieces 114b having a second size that is smaller than the first size, and/or the third plurality of blades 90c may be configured to shred the second shredded pieces 114b into third shredded pieces 114c having a third size that is smaller than the second size. It will be understood that additional or fewer shredder assemblies 16 may be used to shred the waste 14 into a desired size in a series of stages.

The first shredder assembly 16a, the second shredder assembly 16, and/or the third shredder assembly 16c may be offset from one another longitudinally and/or laterally.

As will be understood, though the first, second, and third shredder assemblies 16a, 16b, 16c are shown, additional or fewer shredder assemblies 16 may be used.

In some embodiments, the shredder assembly 16 may comprise a second shaft 52a extending within the housing 60 along the length L of the housing 60, the second shaft 52a rotatable about a third axis 81. In some embodiments, the second shaft 52 may extend within the housing 60 along the width W of the housing 60. The second shaft 52 may be positioned between the top 62 and the bottom 66 of the housing 60 and between the first shaft 52 and the bottom 66 of the housing 60. The shredder assembly 16 may include the second plurality of blades 90b attached to the second shaft 52a, the second plurality of blades 90b comprising at least a third blade 97 and a fourth blade 99 on the second shaft 52a, so as to shred the shredded pieces 114a of the waste 14 into smaller shredded pieces 114b when the second shaft 52 is rotated.

As will be understood, additional shafts and blades may be used to obtain a desired size of shredded pieces 114. Further, the housing 60 may encompass all or some of the components or multiple housings 60 and/or multiple full shredder assemblies 16 may be used in combination. Additionally, the additional shafts 52 may be rotated by the components described herein as rotating the shaft 52 and/or the additional shafts may be mechanically connected to the shaft 52 such that rotation of the shaft 52 causes rotation of the additional shafts.

Returning to FIG. 25, in some embodiments, the waste-volume reduction rig system 10c may include or may be connected to the one or more power sources 208. The one or more power sources may be one or more of bio-fuel generators, diesel generators, gasoline generators, stationary power supplies, solar powered electrical generators, and the like. Power sources 208 may also be attached to or come from separate electrical connections to one or more engines (such as, but not limited to, an engine of the transporter 310). In some embodiments, movement of the vehicle (such as, but not limited to, the transporter 310) may generate power directly or indirectly. For example, movement of the vehicle may power a motor to power the shredder assembly 16 or an axle or friction can directly or indirectly rotate the shaft 52 of the shredder assembly 16.

In some embodiments, the waste-volume reduction rig system 10c may include, or be connected to or connectable to, the conveyor 230. In some embodiments, the conveyor 230 may have telescoping capabilities for storage of the waste 14.

In some embodiments, the waste-volume reduction rig system 10c may include one or more inside conveyor systems 320. In some embodiments, the waste 14 may be fed into one or more of the shredder assemblies 16 via gravity and/or by the inside conveyor system 320. In some embodiments, the waste-volume reduction rig system 10c may have the fluid-bypass 45 connected to the inside conveyor system 320 and/or the conveyor 230. The fluid-bypass 45 may be configured to separate fluids from solids in the waste 14. In some embodiments, the fluids may be directed to flow into a hose for disposal. Depending upon the embodiment, the one or more power sources 208 may be used to power the conveyor 230 and/or the inside conveyor system 320.

The waste-volume reduction rig system 10c may include, or may deposit the shredded pieces 114 of the waste 14 into one or more containers. The containers may include the receiving bag 140 and/or other bag, box, and/or bottle. The containers may be constructed of one or more materials, including but not limited to, Plexiglas, poly, metals, fabrics, glass, and including materials composed of nano technology derived carbons, and the like.

In some embodiments, the waste-volume reduction rig system 10c may include an automatic bagging system 330. The automatic bagging system may comprise one or more of bags (such as the receiving bag 140), boxes, and other means of collecting the shredded pieces 114 of the waste 14.

The waste-volume reduction rig system 10c may include one or more door 340 into the transporter 310.

One or more of the feeder chutes 12 may be positioned on one more of the sides 318, the top 314, or the bottom 316 of the transporter 310.

Figure 26:
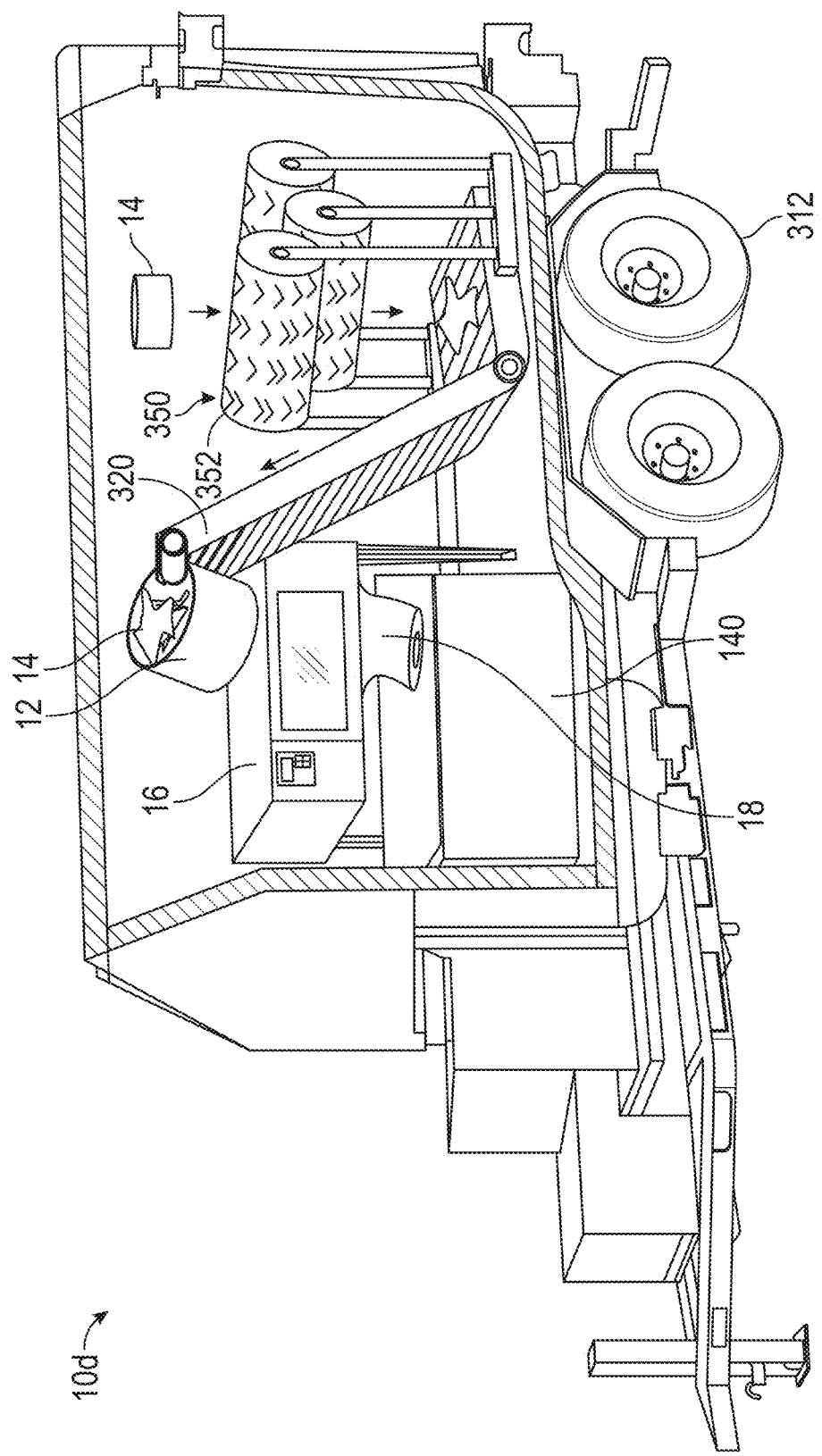
FIG. 26 is a perspective view of another exemplary waste-volume reduction rig system in accordance with the present disclosure.

Turning now to FIG. 26, shown therein is an exemplary embodiment of a waste-volume reduction rig system 10d, which is similar to the waste-volume reduction system 10 and waste-volume reduction rig system 10c, excepted as described. In some embodiments, the waste-volume reduction rig system 10d may include one or more roller systems 350 having a plurality of rollers 352 positioned in relation to one another so as to crush and/or condense the waste 14 between and/or by the rollers 352. The plurality of rollers 352 may be positioned to receive the waste before the shredder assemblies 16 receive the waste.

Figure 27:
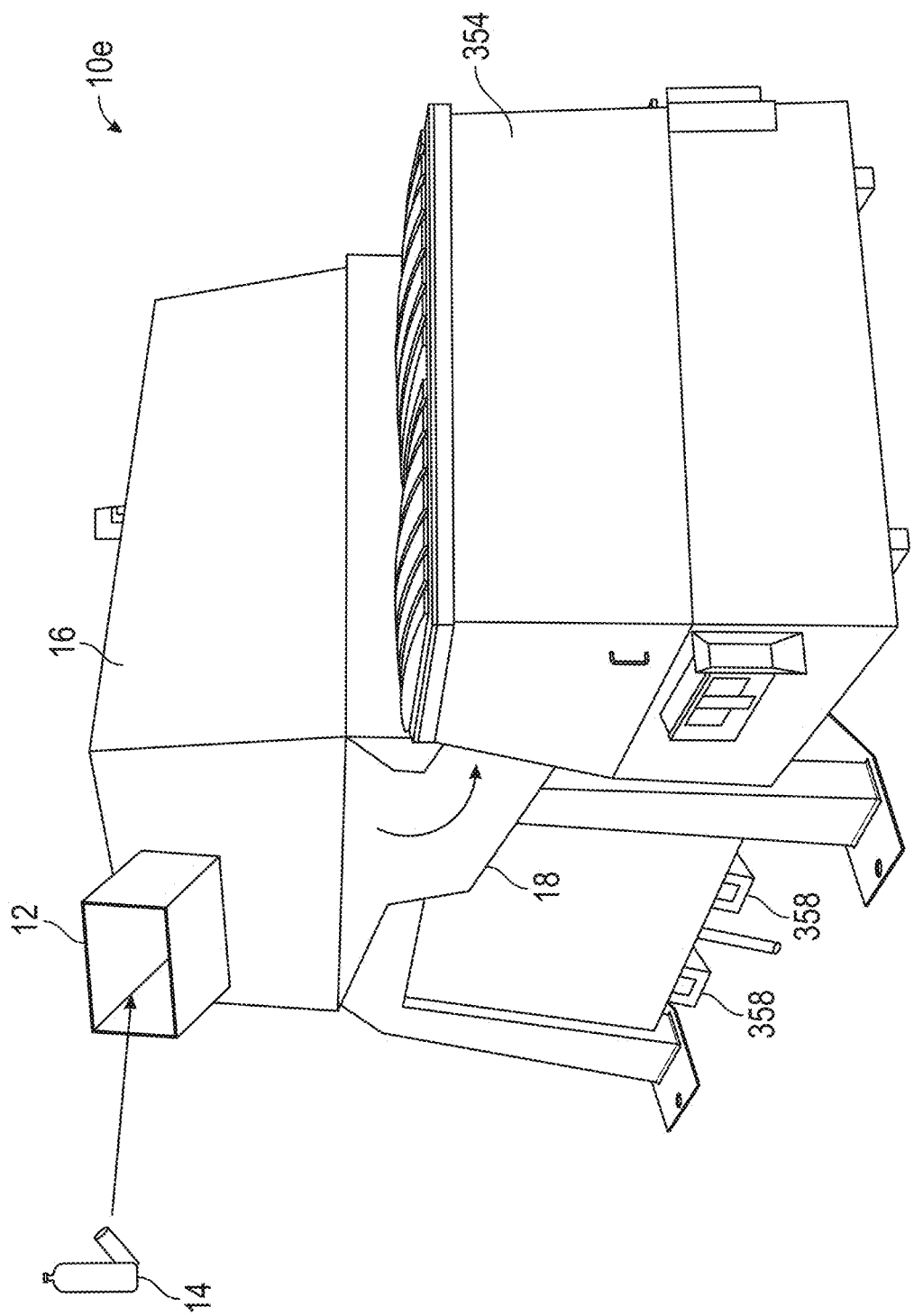
FIG. 27 is a perspective view of an exemplary stationary waste-volume reduction system in accordance with the present disclosure.

Referring now to FIG. 27, a stationary waste-volume reduction rig system 10e is shown that is similar to the waste-volume reduction rig system 10c, 10d in that it may be transported, but the rig system 10e is stationarily positioned to receive the waste 14 from an area, such as parks or rural locations. The stationary waste-volume reduction rig system 10e may further include a detachable pod 354 that contains the shredded pieces 114 of the waste 14 and is portable.

For example, in one embodiment the stationary waste-volume reduction rig system 10e may have a detachable pod 354 for receiving the shredded pieces 114 of the waste 14 that can be unlatched and removed from the rig system 10c, 10d, 10e, such as by a forklift, when full, and another empty pod 354 can be put in its place. Accordingly, the detachable pod 354 and the stationary waste-volume reduction rig system 10e may each have manual or automatic latching devices that are complimentary to each other to secure the detachable pod 354 to the stationary waste-volume reduction rig system 10e. The detachable pod 354 may be any shape or structure that correspondingly engages the stationary waste-volume reduction rig system 10e and receives the shredded pieces 114 of the waste from the exit chute 18. As appreciated by those in the art, the detachable pod 354 may also have machinery adaptations 358 for transport machinery to easily remove the detachable pod 354 and replace it, such as crevices/slots/support structures for use with forklifts.

Figure 28:
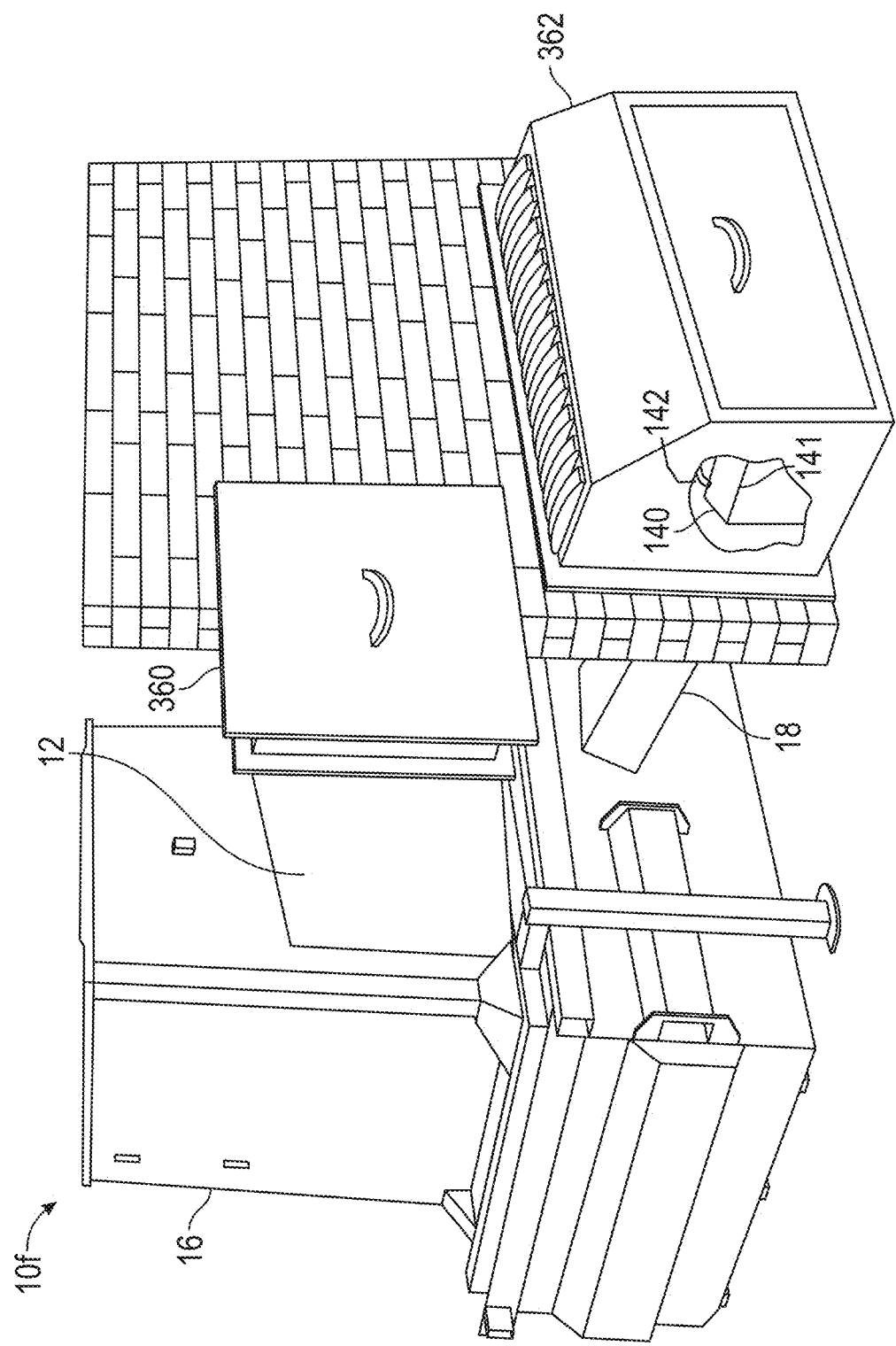
FIG. 28 is a perspective view of another exemplary stationary waste-volume reduction system in accordance with the present disclosure.

In some embodiments, another waste-volume reduction rig system 10f may be similar to the stationary waste-volume reduction rig system 10e, but is at least partially indoors, such as within a convenience store, drug store, or gas station. In an exemplary embodiment, shown in FIG. 28, the rig system 10f may include an in-wall deposit door 360 and/or an in-wall collection drawers 362. The in-wall deposit door 360 and/or in-wall collection drawer 362 may physically connect to the feeder chute 12 and exit chute 18, respectively. The in-wall deposit door 360 and/or in-wall collection drawer 362 may also connect to the motor assembly 200 and/or controller 210 to automatically activate or cease motor activity upon the opening or closing of the in-wall deposit door 360 or the in-wall collection drawer 362. For example, the motor assembly 200 may automatically turn on to grind the waste 14 when the controller 210 detects the in-wall deposit door 360 has been opened to accept the waste 14 and fully closed.

The in-wall deposit door 360 may be, for example, a slot in the wall or a depository mounted within the wall. The in-wall collection drawer 362 may be any shape and volume sufficient to collect large amounts of the shredded pieces 114 of the waste 14 from the exit chute 18. In some cases, the in-wall collection drawer 362 may be replaceable with a new in-wall collection drawer 362 once full, similar to the detachable pod 354. In other cases, the in-wall collection drawer 362 may house containers that collect the shredded pieces 114 of the waste 14, such as boxes, waxed boxes, bags, sacks, the receiving bag 140, or others means, which can then be replaced within the in-wall collection drawer 362 when the container(s) are full.

In some embodiments, the receiving bag 140 is a box with a lid 141, and the in-wall collection drawer 362 is configured to contact and move the lid of the box to a closed position when the drawer 362 is opened. For example, the drawer 362 may have a catch 142 or hook positioned proximate to a top end of the drawer 362 that may engage with the lid 141 of the box to pull or flip the lid from an open position to a closed position.

For exemplary purposes herein, the waste-volume reduction system 10, 10a, 10b and waste-volume reduction rig system 10c, 10d, 10e, 10f may be used interchangeably when referenced regarding any component variations/additions discussed herein. For example, the waste-volume reduction system 10, 10a, 10b and waste-volume reduction rig system 10c, 10d, 10e, 10f may include the feeder chute 12, 12a and/or the sort-feeding chute 12b, the intake fluid-bypass 45 positioned along the exit chute 18, and/or one or more of the conveyors 230.

The waste-volume reduction system 10, 10a, 10b and the waste-volume reduction rig system 10c, 10d, 10e, 10f may incorporate any number of conveyors 230 and inside conveyor systems 320 necessary to accommodate the transport of the waste 14 to the feeder chute 12 and transport of the waste 14 and/or the shredded pieces 114 of the waste 14 to any other components of the system 10, 10a-10f.

Further, some embodiments may include a receiving process for waste 14 that includes one or more carousel modules 368, such as shown in FIG. 29. The carousel module 368 may allow for continuous operation, and may further communicate with the controller 210 to coordinate operation. The carousel module 368 may be positioned horizontally or vertically in relation to the ground, and operate alone or in tandem with one or more of the conveyors 230/conveyor system 320 to suit the environment in which the waste-volume reduction system 10, 10a, 10b or waste-volume reduction rig system 10c, 10d, 10e, 10f operates.

In an exemplary embodiment, as shown in FIG. 29, the carousel module 368 may have a bottom surface that may hinge open to allow the waste 14 to drop through to the feeder chute 12. In some embodiments the carousel module 368 may operate as the feeder chute 12 and may feed the waste 14 directly to the shredder assembly 16.

In some embodiments, the waste-volume reduction system 10, 10a, 10b and/or the waste-volume reduction rig system 10c, 10d, 10e, 10f may be controlled remotely and/or run/maintained using artificial intelligence and/or a virtual process.

In some embodiments, the waste-volume reduction system 10 and/or the waste-volume reduction rig system 10c, 10d, 10e, 10f may include a lock and may be closed and locked, manually and/or automatically, so as to limit use to predetermined or set times. In particular, locks may be used to control access to motors and other components that are in public areas, such as the rig system 10e, 10f in a park or convenience store.

In some embodiments, the waste-volume reduction rig system 10c, 10d, 10e, 10f also includes safety features such as fire/smoke detection, alarms, and water sprinklers. Alarms may indicate component status or condition as well, such as necessary maintenance or component failure.

Figure 30:
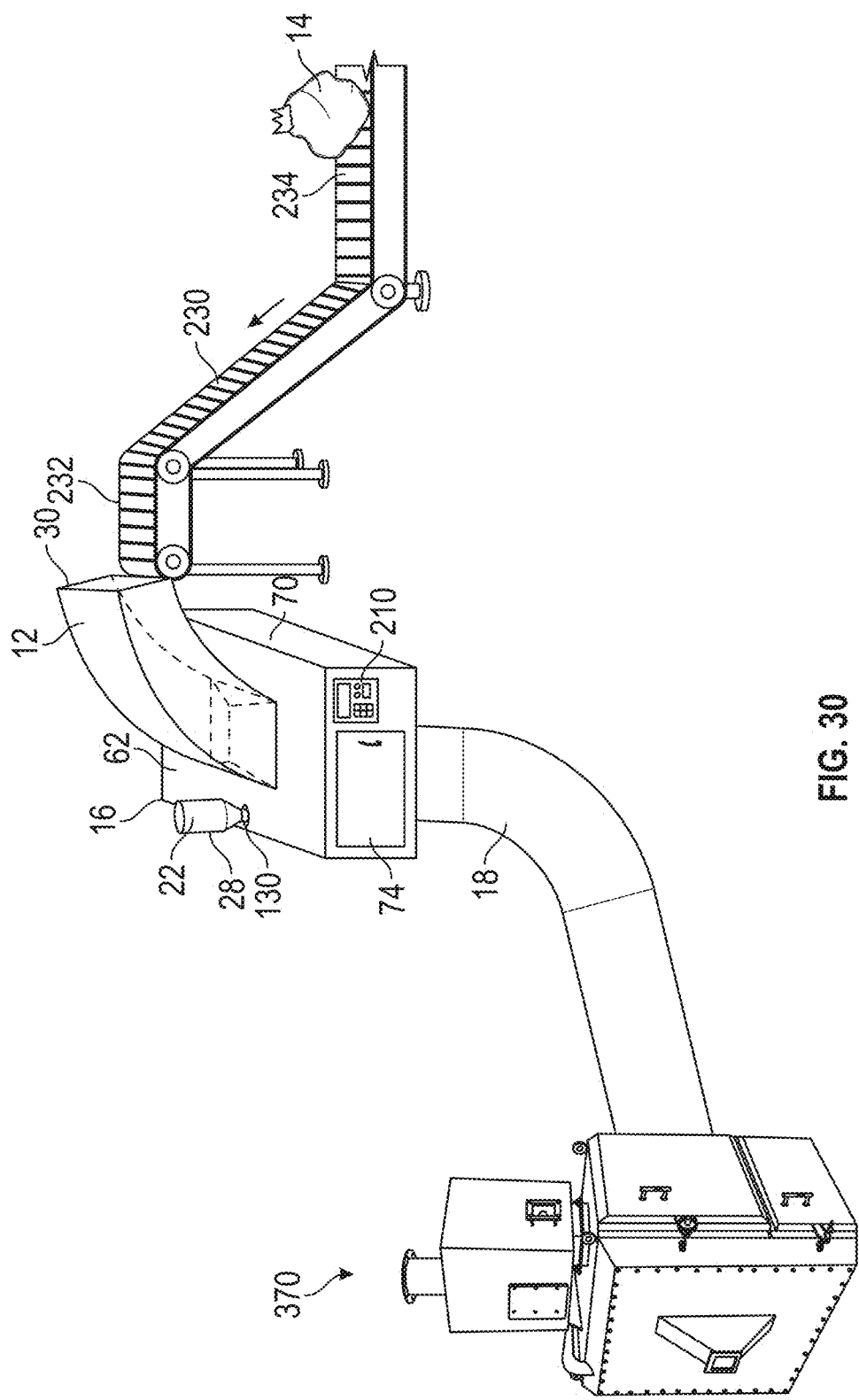
FIG. 30 is a perspective view of components of yet another exemplary waste-volume reduction system in accordance with the present disclosure.

In some embodiments, the waste-volume reduction system 10, 10a, 10b and/or the waste-volume reduction rig system 10c, 10d, 10e, 10f may include an on-site incinerator 370, as illustrated in FIG. 30. The incinerator 370 may be a stationary or mobile incinerator that burns the shredded pieces 114 of the waste 14 to further reduce waste volume. In one embodiment the incinerator 370 is a single chamber that can process around 440 pounds of solid waste per day. Transporting the shredded pieces 114 of the waste 14 to the incinerator 370 may be done manually, or there may be a conveyor that transports the shredded pieces 114 of the waste 14 from the exit chute 18 to the incinerator, as shown in FIG. 30.

In some embodiments, the components of the waste-volume reduction system 10 may be part of one or more kits.

CONCLUSION

Conventionally, trash takes up a disproportionately large amount of space, both at collection and at disposal sites. This inefficiency results in increased transportation costs, including additional fuel, manpower, and equipment, as fewer items can be transported per trip. Trash that is not broken down before disposal also accelerates the rate at which landfill space is used and takes longer to decompose than waste broken into smaller pieces. In accordance with the present disclosure, systems and methods for waste-volume reduction are disclosed that reduce the waste into shredded pieces, that can be more easily and compactly handled, transported, and disposed.

The foregoing description provides illustration and description, but is not intended to be exhaustive or to limit the inventive concepts to the precise form disclosed. Modifications and variations are possible in light of the above teachings or may be acquired from practice of the methodologies set forth in the present disclosure.

Even though particular combinations of features are recited in the claims and/or disclosed in the specification, these combinations are not intended to limit the disclosure. In fact, many of these features may be combined in ways not specifically recited in the claims and/or disclosed in the specification. Although each dependent claim listed below may directly depend on only one other claim, the disclosure includes each dependent claim in combination with every other claim in the claim set.

No element, act, or instruction used in the present application should be construed as critical or essential to the invention unless explicitly described as such.

What is claimed is:

1. A waste-volume reduction system, comprising:
a feeder chute having an intake end, an output end, an interior, and an exterior, the feeder chute configured to channel waste through the interior, wherein at least the intake end of the feeder chute is rotatable about a first axis, wherein the output end of the feeder chute comprises one or more ball bearings;
a shredder assembly, the shredder assembly comprising:
a housing having a length, a top having a first opening, a bottom having a second opening, and a wall extending between the top and the bottom, wherein the first opening of the top is positioned proximate to the output end of the feeder chute and aligned with at least a portion of the interior of the feeder chute so as to accept waste from the feeder chute;
a shaft extending within the housing along the length of the housing, the shaft rotatable about a second axis, the shaft positioned between the top and the bottom of the housing;
a plurality of blades attached to the shaft, the plurality of blades comprising at least a first blade and a second blade, wherein the first blade is rotationally offset about the second axis on the shaft from the second blade, so as to shred the waste into shredded pieces when the shaft rotates; and
a plurality of cleaning arms attached to the interior of the housing and positioned such that at least a portion of the plurality of blades passes between two or more of the cleaning arms when the plurality of blades is rotated within the housing by the shaft;
an anti-bacterial agent reservoir positioned proximate to the shredder assembly and configured to contain one or more anti-bacterial agents, the anti-bacterial agent reservoir having an applicator configured to disperse the one or more anti-bacterial agents from the anti-bacterial agent reservoir onto the shredded pieces of the waste; and
an exit chute having an entry end aligned with the second opening of the bottom of the housing of the shredder assembly so as to accept the shredded pieces of the waste from the shredder assembly, the exit chute having an exit end configured to dispense the shredded pieces of the waste.

2. The system of claim 1, wherein the output end of the feeder chute comprises one or more lock that is configured to lock the feeder chute into place rotationally.

3. The system of claim 1, comprising:
a motor assembly configured to rotate the shaft of the shredder assembly.

4. The system of claim 1, comprising:
a conveyor having a first end and a second end, the first end positioned proximate to the intake end of the feeder chute so as to channel the waste into the intake end of the feeder chute.

5. The system of claim 1, comprising a removable container configured to receive the shredded pieces of the waste, the removable container comprising one or more of a box, a waxed box, a sack, and a bag.

6. A waste-volume reduction system, comprising:
a feeder chute having an intake end, an output end, an interior, and an exterior, the feeder chute configured to channel waste through the interior, wherein at least the intake end of the feeder chute is rotatable about a first axis;
a shredder assembly, the shredder assembly comprising:
a housing having a length, a top having a first opening, a bottom having a second opening, and a wall extending between the top and the bottom, wherein the first opening of the top is positioned proximate to the output end of the feeder chute and aligned with at least a portion of the interior of the feeder chute so as to accept waste from the feeder chute;
a shaft extending within the housing along the length of the housing, the shaft rotatable about a second axis, the shaft positioned between the top and the bottom of the housing;
a plurality of blades attached to the shaft, the plurality of blades comprising at least a first blade and a second blade, wherein the first blade is rotationally offset about the second axis on the shaft from the second blade, so as to shred the waste into shredded pieces when the shaft rotates; and
a plurality of cleaning arms attached to the interior of the housing and positioned such that at least a portion of the plurality of blades passes between two or more of the cleaning arms when the plurality of blades is rotated within the housing by the shaft;
an anti-bacterial agent reservoir positioned proximate to the shredder assembly and configured to contain one or more anti-bacterial agents, the anti-bacterial agent reservoir having an applicator configured to disperse the one or more anti-bacterial agents from the anti-bacterial agent reservoir onto the shredded pieces of the waste;
an exit chute having an entry end aligned with the second opening of the bottom of the housing of the shredder assembly so as to accept the shredded pieces of the waste from the shredder assembly, the exit chute having an exit end configured to dispense the shredded pieces of the waste; and a drawer and a removable box within the drawer, the removable box having a lid, the drawer configured to contact and move the lid of the removable box to a closed position when the drawer is opened.

7. The system of claim 1, comprising:
a motor assembly configured to rotate the shaft of the shredder assembly; and
a controller in communication with the motor assembly, the controller configured to change the motor assembly from an active state to a passive state, the controller having an input interface configured to accept control inputs from a user.

8. The system of claim 1, wherein the shaft of the shredder assembly has a polygonal cross section, and wherein one or more of the plurality of blades of the shredder assembly has a complimentary polygonal opening configured to accept the shaft.

9. The system of claim 1, wherein the shaft of the shredder assembly is a first shaft and the plurality of blades of the shredder assembly is an initial plurality of blades, and wherein the shredder assembly comprises:
a second shaft extending within the housing along the length of the housing, the second shaft rotatable about a third axis, the second shaft positioned between the top and the bottom of the housing and between the first shaft and the bottom of the housing; and
a secondary plurality of blades attached to the second shaft, the plurality of blades comprising at least a third blade and a fourth blade on the second shaft, so as to shred the shredded pieces of the waste into smaller shredded pieces when the second shaft rotates.

10. A method for waste-volume reduction, comprising:
feeding waste into a feeder chute having an intake end, an output end, an interior, and an exterior, the feeder chute configured to channel the waste through the interior, wherein at least the intake end of the feeder chute is rotatable about a first axis, wherein the output end of the feeder chute comprises one or more ball bearings;
rotating the output end of the feeder chute utilizing the one or more ball bearings in order to accept waste into the feeder chute;
shredding the waste into shredded pieces with a shredder assembly, the shredder assembly comprising:
a housing having a length, a top having a first opening, a bottom having a second opening, and a wall extending between the top and the bottom, wherein the first opening of the top is positioned proximate to the output end of the feeder chute and aligned with at least a portion of the interior of the feeder chute so as to accept the waste from the feeder chute;
a shaft extending within the housing along the length of the housing, the shaft rotatable about a second axis, the shaft positioned between the top and the bottom of the housing;
a plurality of blades attached to the shaft, the plurality of blades comprising at least a first blade and a second blade, wherein the first blade is rotationally offset about the second axis on the shaft from the second blade, so as to shred the waste into the shredded pieces when the shaft rotates; and
a plurality of cleaning arms attached to the interior of the housing and positioned such that at least a portion of the plurality of blades passes between two or more of the cleaning arms when the plurality of blades is rotated within the housing by the shaft;
dispersing one or more anti-bacterial agents from a reservoir positioned proximate to the shredder assembly, the reservoir having an applicator configured to disperse the one or more anti-bacterial agents from the reservoir onto the shredded pieces of the waste; and
dispensing the shredded pieces of waste from an exit chute having an entry end aligned with the second opening of the bottom of the housing of the shredder assembly so as to accept the shredded pieces of the waste from the shredder assembly, the exit chute having an exit end configured to dispense the shredded pieces of the waste.

11. The method of claim 10, comprising, locking the feeder chute in place rotationally with one or more lock positioned on the output end of the feeder chute.

12. The method of claim 10, wherein the shaft of the shredder assembly is rotated with a motor assembly.

13. The method of claim 10, comprising:
utilizing a conveyor so as to channel the waste into the intake end of the feeder chute, the conveyor having a first end and a second end, the first end positioned proximate to the intake end of the feeder chute.

14. The method of claim 10, comprising:
placing a removable container proximate to the exit end of the exit chute, the removable container having a top, a bottom, and wall extending between the top and the bottom, the top, the bottom, and the wall cooperating to create a waste-receiving interior, wherein the wall has an opening configured to accept the shredded pieces of the waste.

15. A method for waste-volume reduction, comprising:
feeding waste into a feeder chute having an intake end, an output end, an interior, and an exterior, the feeder chute configured to channel the waste through the interior, wherein at least the intake end of the feeder chute is rotatable about a first axis;
shredding the waste into shredded pieces with a shredder assembly, the shredder assembly comprising:
a housing having a length, a top having a first opening, a bottom having a second opening, and a wall extending between the top and the bottom, wherein the first opening of the top is positioned proximate to the output end of the feeder chute and aligned with at least a portion of the interior of the feeder chute so as to accept the waste from the feeder chute;
a shaft extending within the housing along the length of the housing, the shaft rotatable about a second axis, the shaft positioned between the top and the bottom of the housing;
a plurality of blades attached to the shaft, the plurality of blades comprising at least a first blade and a second blade, wherein the first blade is rotationally offset about the second axis on the shaft from the second blade, so as to shred the waste into the shredded pieces when the shaft rotates; and
a plurality of cleaning arms attached to the interior of the housing and positioned such that at least a portion of the plurality of blades passes between two or more of the cleaning arms when the plurality of blades is rotated within the housing by the shaft;
dispersing one or more anti-bacterial agents from a reservoir positioned proximate to the shredder assembly, the reservoir having an applicator configured to disperse the one or more anti-bacterial agents from the reservoir onto the shredded pieces of the waste;

dispensing the shredded pieces of waste from an exit chute having an entry end aligned with the second opening of the bottom of the housing of the shredder assembly so as to accept the shredded pieces of the waste from the shredder assembly, the exit chute having an exit end configured to dispense the shredded pieces of the waste, wherein the exit chute is positioned to dispense the shredded pieces of waste into a box having a lid in an open position, the box positioned in a drawer, the drawer having a catch mechanism; and opening the drawer thereby causing the catch mechanism to pull the lid of the box to a closed position.

16. The method of claim 10, comprising:

changing, with a controller in communication with a motor assembly, the motor assembly from an active state to a passive state, the controller having an input interface configured to accept control inputs from a user.

17. The method of claim 10, wherein the shaft of the shredder assembly has a polygonal cross section, and wherein one or more of the plurality of blades of the shredder assembly has a complimentary polygonal opening configured to accept the shaft.

18. The method of claim 10, wherein the shaft of the shredder assembly is a first shaft and the plurality of blades of the shredder assembly is an initial plurality of blades, and wherein the shredder assembly comprises: a second shaft extending within the housing along the length of the housing, the second shaft rotatable about a third axis, the second shaft positioned between the top and the bottom of the housing and between the first shaft and the bottom of the housing; and a second plurality of blades attached to the second shaft, the second plurality of blades comprising at least a third blade and a fourth blade on the second shaft; and the method comprising rotating the second shaft to shred the shredded pieces of waste into smaller shredded pieces of waste with the second plurality of blades as the second shaft rotates.

* * * * *